(12) United States Patent
Chu et al.

(10) Patent No.: US 11,275,354 B2
(45) Date of Patent: Mar. 15, 2022

(54) SYSTEMS, METHODS AND FILE FORMAT FOR 3D PRINTING OF MICROSTRUCTURES

(71) Applicant: OPT Industries, Inc., Medford, MA (US)

(72) Inventors: Kai-Hong Anthony Chu, Boston, MA (US); Jifei Ou, Cambridge, MA (US); Andre Schmeing, Aachen (DE)

(73) Assignee: OPT Industries, Inc., Medford, MA (US)

( * ) Notice: Subject to any disclaimer, the term of this patent is extended or adjusted under 35 U.S.C. 154(b) by 0 days.

(21) Appl. No.: 17/211,658

(22) Filed: Mar. 24, 2021

(65) Prior Publication Data

US 2021/0298464 A1  Sep. 30, 2021

Related U.S. Application Data

(60) Provisional application No. 63/058,782, filed on Jul. 30, 2020, provisional application No. 62/994,582, filed on Mar. 25, 2020.

(51) Int. Cl.
*A46B 9/02* (2006.01)
*A61B 10/00* (2006.01)
(Continued)

(52) U.S. Cl.
CPC ............ *G05B 19/4099* (2013.01); *A41G 5/02* (2013.01); *A45D 34/042* (2013.01); *A46B 1/00* (2013.01);
(Continued)

(58) Field of Classification Search
CPC ........ A61B 10/0045; A61B 2010/0074; A61B 2090/037; A61B 2010/0216;
(Continued)

(56) References Cited

U.S. PATENT DOCUMENTS 2,510,490 A * 6/1950 Ager .................. A61F 13/38
604/1
5,715,559 A * 2/1998 Mitri .................. A61F 13/38
15/118
(Continued)

FOREIGN PATENT DOCUMENTS

CN       1589697 A  *  3/2005  ........... A46D 1/0238
WO  WO-2014207598 A1 * 12/2014  ......... A61B 10/0045

OTHER PUBLICATIONS

Invitation to Pay Additional Fees dated May 27, 2021 in connection with International Application No. PCT/US2021/023962.
(Continued)

*Primary Examiner* — Susan S Su
(74) *Attorney, Agent, or Firm* — Wolf, Greenfield & Sacks, P.C.

(57) ABSTRACT

Systems, methods, and new file formats are provided for printing 3D microstructures. In some implementations, a new file format is provided that defines 3D objects by a wireframe model expressed as a collection of wires. Because wires and their parameters are defined within the new file format, objects may be processed more efficiently and quickly to support 3D rendering operations. Such methods may be used to print new articles, such as eyelashes, bushes, swabs and other novel items.

36 Claims, 52 Drawing Sheets
(39 of 52 Drawing Sheet(s) Filed in Color)

(51) Int. Cl.
| | |
|---|---|
| *A61F 13/38* | (2006.01) |
| *G05B 19/4099* | (2006.01) |
| *B33Y 50/02* | (2015.01) |
| *B33Y 50/00* | (2015.01) |
| *B33Y 80/00* | (2015.01) |
| *A41G 5/02* | (2006.01) |
| *A45D 34/04* | (2006.01) |
| *A46B 1/00* | (2006.01) |
| *A46B 9/08* | (2006.01) |
| *B29C 64/393* | (2017.01) |
| *G06T 17/20* | (2006.01) |

(52) U.S. Cl.
CPC .............. *A46B 9/021* (2013.01); *A46B 9/026* (2013.01); *A46B 9/08* (2013.01); *A61B 10/0045* (2013.01); *A61F 13/38* (2013.01); *B29C 64/393* (2017.08); *B33Y 50/00* (2014.12); *B33Y 50/02* (2014.12); *B33Y 80/00* (2014.12); *G06T 17/20* (2013.01); *A46B 2200/1046* (2013.01); *G05B 2219/35134* (2013.01); *G05B 2219/49023* (2013.01)

(58) Field of Classification Search
CPC ... A61B 10/0051; A46B 9/00–12; A46B 9/08; A46B 9/021; A46B 9/026; B01L 3/5029; A61F 13/38
See application file for complete search history.

(56) References Cited

U.S. PATENT DOCUMENTS

| | | | |
|---|---|---|---|
| 9,923,266 | B1 | 3/2018 | Casperson et al. |
| 10,869,782 | B2 * | 12/2020 | Giaquinto ............... A61F 13/38 |
| 2005/0267395 | A1 * | 12/2005 | Mangold ................ D04H 1/425 604/1 |
| 2012/0296355 | A1 * | 11/2012 | Burres .................. A61F 11/006 606/162 |
| 2015/0018861 | A1 * | 1/2015 | Olson ................... A61F 11/006 606/162 |
| 2016/0325505 | A1 | 11/2016 | Ou et al. |
| 2017/0014111 | A1 | 1/2017 | Hulseman et al. |
| 2018/0098829 | A1 | 4/2018 | Fisker et al. |
| 2021/0146644 | A1 | 5/2021 | Kita et al. |

OTHER PUBLICATIONS

Ou et al., Method of 3D Printing Micro-pillar Structures on Surfaces. UIST '15 Adjunct. Nov. 8-11, 2015; pp. 59-60.

* cited by examiner

| | InstaSwab™ | Leading flocked fiber swab | Cotton Swab |
|---|---|---|---|
| Absorption volume (uL)[1] | 92 ± 11 | 84 ± 13 | 122 ± 13 |
| Liquid releasing ratio[2] | 83 ± 4 % | 86 ± 3 % | 25 ± 5 % |
| Bacteria elution ($10^4$ CFU/mL)[3] | > 500 | ~27 | NA |
| Bacteria elution ($10^6$ CFU/mL)[3] | 22 ± 14 | 0 | NA |
| PCR compatibility | Compatible | Compatible | Contested |

FIG. 36D

[1]: Based on NIH protocol NS_Adsorption_Protocol_1.1 "Absorption Test Protocol for Nasal Swabs".
[2]: Liquid/solid separation ratio is defined as the weight loss after gently rolling the sample-loading swabs against an absorbing surface for ten seconds.
[3]: Based on M40-A2 and NIH protocol NS_Elution_Protocol_1.1 "Elution Test Protocol for Nasal Swabs".
[4]: Based on Copan report: https://www.copanusa.com/wp-content/uploads/2019/08/671562638015_Final_2019_ASM_poster.pdf

SYSTEMS, METHODS AND FILE FORMAT FOR 3D PRINTING OF MICROSTRUCTURES

RELATED APPLICATIONS

This application is a Non-Provisional of Provisional (35 USC 119(e)) of U.S. Application Ser. No. 62/994,582 filed Mar. 25, 2020, entitled "SYSTEMS, METHODS AND FILE FORMAT FOR 3D PRINTING OF MICROSTRUCTURES" and this application is a Non-Provisional of Provisional (35 USC 119(e)) of U.S. Application Ser. No. 63/058,782 filed Jul. 30, 2020, entitled "SYSTEMS, METHODS AND FILE FORMAT FOR 3D PRINTING OF MICROSTRUCTURES". The entire contents of these applications are incorporated herein by reference in their entirety.

NOTICE OF MATERIAL SUBJECT TO COPYRIGHT PROTECTION

Portions of the material in this patent document are subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

There are many different types of 3D printing technologies that are used to construct a three-dimensional object from a digital 3D model. 3D printing processes can use a variety of processes in which material is deposited, joined, or solidified using computer control to create objects using plastics, liquids or powder grains, among other materials.

SUMMARY

Recent 3D printing technology can allow complex geometries that are difficult or impossible to make with conventional manufacturing technologies. In some embodiments, the inventors appreciate that high resolution stereolithography 3D printing, specifically Digital Light Processing (DLP) printing technology may be used that allows printing resolution of less than 100 μm. The high-resolution 3D printing can allow one to produce intricate structures to reduce object weight, construct metamaterials, realize biomimicry design or simply achieve aesthetic surface textures.

Although the resolution of recent 3D printers has been improving, it can be impractical to directly print extremely dense microstructures such as fur, feather, microlattices, or woven fabric. This can be due primarily to the lack of an efficient digital representation of CAD models with fine material structure. In general, 3D printers and related CAD/CAM design softwares are typically optimized for processing medium to large scale solid objects. These objects could be represented faithfully with triangulated mesh, which could be transferred between parties as .stl or other mesh-type data formats. They are also characterized by their smooth finish, which has become a prime feature in latest 3D printers. However, when it comes to representing and processing dense microstructures, such files that represent these microstructures become extremely large and slicing such complex structures for printing can also be computationally expensive.

In some embodiments described herein, systems, methods and new file formats are provided for printing 3D microstructures. Such microstructures may have, for example, high precision features from 0.001 to 5 mm. These features could include surface relief texture, three dimensional woven structures, lattices, fur or feather-like structures. These small features often require high fidelity to capture the nuance of softness, stretchiness and tactility. With conventional CAD approaches, a precise 3D model of every single strand could in theory create a high-fidelity representation of these nuances, but such a file would be extraordinarily large and would be difficult to process and print. For instance, a typical fur sample might contain thousands of hairs per square inch, meaning a simple garment design with millions of triangles could be cumbersome and impractical.

To address this dilemma between file economy and geometric fidelity, a new file format used to represent 3D microstructures (referred to herein as a MESO format (.MESO or .meso)) is provided to serve as an advanced interface between designers and 3D printers. In some embodiments, this file exchange format establishes efficient workflows for computational design and data transfer within our printing ecosystem to get from sketches and designs to finished prints.

In some embodiments, a .meso file format and slicing process is provided that open up a new space for material design and engineering. One goal is to support designers and engineers to model dense microstructures that were previously considered computationally expensive or impossible. Specifically, such dense structures can be used for different applications as outlined further below. Such embodiments may permit one or more improvements including:

Reducing material usage and weight: bulk solid structures can be replaced by carefully designed microlattice structures. In some embodiments, the geometry of the lattice determines the overall mechanical property of the design. In this way, manufacturers can reduce the material used for 3D printing, and reduce the weight of the overall design.

Mechanical metamaterials: by incorporating micro compliant, joint or hinge structures, the ability is provided to design and manufacture mechanical metamaterials that exhibit negative Poisson ratio (e.g., auxetic structures or materials that become thicker in a perpendicular direction to the applied force and thus have high energy absorption and fracture resistance). In this way, new mechanical elements exhibiting certain structural properties may be created.

Biomimicry design: natural materials can be superior to artificial ones, largely due to their hierarchical structures. Materials like fur or feathers are difficult to be modelled with the traditional CAD software and precisely replicated with other manufacturing methods. In some embodiments described herein, the complexity of the modelling is drastically reduced while maintaining the density and fine details of such structures for 3D printing.

Customized surface texture: Many physical products that are used in commerce contains surface texture such as wrinkles, dimples, bumps, relieves, etc. According to some embodiments, one can design and manufacture such textures at extreme high resolution. Such texture can be easily customized individually, rather than being mass produced.

According to one aspect, a data format for representing a 3D object comprising of a data structure is provided. The format comprises of node information identifying a plurality of 3D coordinates within a 3D wireframe object, wire information identifying a plurality of nodes that collectively identify a wire object within the 3D wireframe object and shell information identifying a surface to which the wire object attaches, wherein interpretation of the data structure is used to control a 3D printing operation. According to one embodiment, the data structure further comprises of a populate function that defines a repetitive duplication of the wire object to multiple points on the surface. According to one embodiment, the data structure further comprises of a blended function that is adapted to blend at least two geometries. According to one embodiment, the data structure further comprises of mesh information describing a legacy mesh geometry. According to one embodiment, the data structure further comprises of a branch function that describes one or more child objects attached to the wire object. According to one embodiment, the data structure further comprises of a parameter that controls at least one of a thickness, shape and/or twist of the wire object. According to one embodiment, the data format, when received and interpreted by a computer system, renders a representation of the 3D object. According to one embodiment, the data structure is used to generate a 3D swab or applicator. According to one embodiment, the data structure is used to generate a blended design of at least two designs.

According to one aspect, a method for processing a digital representation of a 3D object is provided. The method comprises of providing a wireframe representation of the 3D object, the wireframe representation defining at least one wire, determining a slice of the 3D object to be processed, determining for the determined slice, at least one intersection point defining an intersection of the at least one wire of the wireframe representation with the slice of the 3D object, and determining for the intersection point, a corresponding shape relating to the intersection point to be rendered. According to one embodiment, the act of the corresponding shape relating to the intersection point to be rendered further comprises of determining, based on at least one parameter of the at least one wire, the corresponding shape. According to one embodiment, at least one parameter includes at least one or more of the group comprising thickness, shape and twist of the wire object. According to one embodiment, the act of determining the corresponding shape relating to the intersection point to be rendered further comprises of determining, the corresponding shape based on an angle of intersection between the slice and the at least one wire. According to one embodiment, the act of determining the corresponding shape relating to the intersection point to be rendered further comprises of determining, the corresponding shape based on an angle of intersection between the slice and a shape of the at least one wire. According to one embodiment, the method further comprises of determining at least one different slice of the 3D object to be processed, and for the slice and the at least one different slice, processing them in parallel by different processing entities. According to one embodiment, the different processing entities are provided information regarding any lines of the wireframe representation that intersect the associated slice to be processed. According to one embodiment, the act of slicing is performed as part of a printing step. According to one embodiment, the method further comprises of a process for determining, for at least one portion of the 3D object, a mesh representation, and combining a slice of the mesh representation with a corresponding slice of the wireframe representation to form a combined slice. According to one embodiment, the method further comprises of an act of using vector space to calculate, for each slice of the 3D object to be processed, a plurality of lines that intersect a corresponding slice of the 3D object. According to one aspect, the method further comprises of using linear equations to determine the plurality of lines that intersect the corresponding slice of the 3D object. According to one aspect, the method further comprises of an act of determining, for each slice of the 3D object, a set of intersection points that represent lines of the wireframe that intersect a respective slice of the 3D object.

According to one aspect, a method for processing a digital representation of a 3D object is provided. The method comprises of providing a wireframe representation of the 3D object, segmenting the wireframe representation into a plurality of chunks, assigning each one of the plurality of chunks to a corresponding processing entity, and rendering each one of the plurality of chunks, substantially in parallel, by the corresponding processing entity. According to one embodiment, the method further comprises of the act of segmenting the wireframe representation into the plurality of chunks further comprises an act of determining, for at least one of the plurality of chunks, a subset of wire objects of the wireframe representation that intersect with the at least one of the plurality of chunks. According to one embodiment, the method further comprises of an act of determining a representation of the at least one of the plurality of chunks of the wireframe representation. According to one embodiment, the method further comprises of an act of providing the representation of the at least one of the plurality of chunks of the wireframe representation to its assigned processing entity. According to one embodiment, the method further comprises of an act of providing, for the at least one of the plurality of chunks, line information to its assigned processing entity, the line information relating to lines that intersect the at least one of the plurality of chunks. According to one embodiment, the method further comprises of an act of merging each one of the rendered plurality of chunks into a model that represents the 3D object. According to one embodiment, the method further comprises of representing a wire of the wireframe representation as a series of nodes. According to one embodiment, the method further comprises of representing the wire by a plurality of parameters comprising at least one of thickness, shape and twist of the wire.

According to one aspect, a 3D-printed swab or applicator is provided. The swab or applicator comprises of a bulb having an interior lattice structure that provides structural strength and fluid retention, a reinforced net structure upon the interior lattice structure that contributes to the shape of the bulb and absorbs fluid, a plurality of hairs projecting from the reinforced net structure; and a handle connected to the bulb. According to one embodiment, the handle comprises of parallel strands of wires which are bound together and reinforced by loops between the strands. According to one embodiment, the handle comprises of gridded shaft wall structures and an interior shearing reinforcement element. According to one embodiment, the handle comprises of a break point having a reduced diameter of the parallel strands. According to one embodiment, the hairs are reinforced near their mid-section. According to one embodiment, the hairs are arranged in a spiral array. According to one embodiment, the interior lattice structure is contiguous between the bulb and the handle. According to one embodiment, the interior lattice structure is printed by a shell offset from a free-form curve. According to one embodiment, the hairs have a diameter less than about 100 μm. According to one embodiment, the swab is defined by a data structure including a plurality of wire information, the wire information identifying a plurality of nodes that collectively identify at least one wire object.

According to one aspect a 3D-printed swab or applicator is provided. The applicator comprises of a bulb, and a shaft, wherein the bulb includes an internal core as the extension of the shaft, wherein the internal core connects the bulb to the shaft and provides rigidity to the swab or applicator. According to one embodiment, the bulb comprises a radial array of hairs stemming from internal core. According to one embodiment, the radial array of hairs are spaced between approximately 50 um to approximately 200 um. According to one embodiment, the bulb comprises a primary exterior net structure upon interior a hair structure that contributes to the shape of the bulb and absorbs fluid. According to one embodiment, the bulb comprises a secondary internal net structure nested between exterior net and internal core that provide additional rigidity. According to one embodiment, the bulb comprises a plurality of hairs projecting from the primary exterior net structure. According to one embodiment, the shaft comprises a primary structure made up of line element in a diamond grid pattern in a cylindrical form. According to one embodiment, the shaft comprises a secondary structure made up of an internal spiraling surface attached to the diamond grid pattern, that provides internal shearing resistance. According to one embodiment, the shaft comprises a texture finish made up of a thinner line element spiraling on the exterior to provide refined finishing.

According to one aspect, a 3D-printed applicator is provided. The applicator comprises of a bulb having an interior lattice structure that provides structural strength, a plurality of bristles projecting from the interior lattice structure, a plurality of reinforcement wires connected to the bristles at a location along a length of the bristles, and a handle connected to the bulb. According to one embodiment, the location along length of the bristles is near the mid-point of the bristles. According to one embodiment, a length of a bristle is limited such that the bristle is confined within a bounding geometry. According to one embodiment, a diameter of each bristle is individually specified in a meso file. According to one embodiment, the bristles have a diameter that is less than about 100 µm. According to one embodiment, the applicator is defined by a data structure including a plurality of wire information, the wire information identifying a plurality of nodes that collectively identify at least one wire object.

According to one aspect, a method for designing a fabric or article for 3D printing is provided. The method comprises of generating a first design represented by a first file comprising a plurality of parameters having a first set of values, generating a second design represented by a second file having a second set of values for the parameters, and interpolating values of the parameters between the first value and the second value to generate a third design that is a blend of the first design and the second design, wherein the third design is a fabric or article suitable for 3D printing. According to one embodiment, the first design and second design are not represented by a mesh of triangular elements. According to one embodiment, the first and second designs have a similar topography. According to one embodiment, the fabric is fur, feathers, lattices, or woven. According to one embodiment, the fabric has a smallest length scale of about 100 µm. According to one embodiment, the fabric has at least 1,000 hairs per square inch. According to one embodiment, the parameters are selected from a diameter of a fiber, a twisting angle of a fiber, a cross sectional profile of a fiber, or any combination thereof. According to one embodiment, the designs comprise shared vertices stored in a list of shared points. According to one embodiment, the act of interpolating further comprises determining applying a weighted average between the first value and the second value to generate the third design. According to one embodiment, the method further comprises for the 3D article, adjusting the weighted average over multiple instances for generating third designs. According to one embodiment, the method further comprises of providing indices associated with first design, applying a transformation matrix to determine the second design, providing a weight value indicating at least a weighted portion of at least one of the first geometry or the second geometry; and applying a weighted average using the weight value to determine the third design.

According to one aspect, a method for designing a fabric or article for 3D printing is provided. The method comprises of providing a design characterized by a file comprising a list of vertices that define a plurality of fibers and a set of parameters which define features of the fibers; and selecting a set of values for the parameters that result in a desired property for the design when 3D-printed. According to one embodiment, the design is repeated or tiled when 3D printed. According to one embodiment, the parameter is a diameter of a fiber, a twisting angle of a fiber, a cross sectional profile of a fiber, or any combination thereof. According to one embodiment, the parameter is a branching function. According to one embodiment, the design has each fiber defined by a separate wire frame and individual value of the parameter. According to one embodiment, the design does not define each fiber by a separate wire frame. According to one embodiment, the fibers are represented as a populate function of shell surfaces. According to one embodiment, the data structure further comprises of a volumetric mapping function. According to one embodiment, the data structure further comprises of an array of vertices of the wireframe object. According to one embodiment, the method further comprises information identifying vertices that define a central polyline spine of the wire object. According to one embodiment, the data structure further comprises of a diameter of the wire object at each of the vertices. According to one embodiment, the data structure further comprises of information identifying a normal direction of a start face at a start point. According to one embodiment, the data structure further comprises of rotation information of the wire object along its vertices. According to one embodiment, the method further comprising acts of segmenting the wireframe representation into a plurality of chunks, assigning each one of the plurality of chunks to a corresponding processing entity, and rendering each one of the plurality of chunks, substantially in parallel, by the corresponding processing entity. According to one embodiment, the act of segmenting the wireframe representation into the plurality of chunks further comprises of an act of determining, for at least one of the plurality of chunks, a subset of wire objects of the wireframe representation that intersect with the at least one of the plurality of chunks. According to one embodiment, the method further comprises of an act of determining a representation of the at least one of the plurality of chunks of the wireframe representation. According to one embodiment, the method further comprises of an act of providing the representation of the at least one of the plurality of chunks of the wireframe representation to its assigned processing entity. According to one embodiment, the method further comprises of an act of providing, for the at least one of the plurality of chunks, line information to its assigned processing entity, the line information relating to lines that intersect the at least one of the plurality of chunks. According to one embodiment, the method further comprises of an act of merging each one of the rendered plurality of chunks into a model that represents the 3D object. According to one embodiment, the method further comprises of representing a wire of the wireframe representation as a series of nodes. According to one embodiment, the method further comprises of representing the wire by a plurality of parameters comprising at least one of thickness, shape and twist of the wire.

It should be understood that all combinations of the foregoing concepts and additional concepts discussed in greater detail below (provided such concepts are not mutually inconsistent) are contemplated as being part of the inventive subject matter disclosed herein. In particular, all combinations of subject matter within this disclosure are contemplated as being part of the inventive subject matter disclosed herein. Also, it should be understood that one or more 3D printing systems may be used to implement the one or more systems, methods and file formats to 3D print such microstructures. For example, some embodiments may be used in conjunction with one or more systems described in U.S. patent application Ser. No. 16/552,382, filed Aug. 27, 2019, incorporated herein in its entirety by reference. However, it should be understood that other printer methods and systems may be used with embodiments as described herein.

Still other aspects, examples, and advantages of these exemplary aspects and examples, are discussed in detail below. Moreover, it is to be understood that both the foregoing information and the following detailed description are merely illustrative examples of various aspects and examples, and are intended to provide an overview or framework for understanding the nature and character of the claimed aspects and examples. Any example disclosed herein may be combined with any other example in any manner consistent with at least one of the objects, aims, and needs disclosed herein, and references to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF THE FIGURES

The patent or application file contains at least one drawing executed in color. Copies of this patent or patent application publication with color drawing(s) will be provided by the Office upon request and payment of the necessary fee.

Various aspects of at least one embodiment are discussed herein with reference to the accompanying figures, which are not intended to be drawn to scale. The figures are included to provide illustration and a further understanding of the various aspects and embodiments and are incorporated in and constitute a part of this specification but are not intended as a definition of the limits of the invention. Where technical features in the figures, detailed description or any claim are followed by reference signs, the reference signs have been included for the sole purpose of increasing the intelligibility of the figures, detailed description, and/or claims. Accordingly, neither the reference signs nor their absence are intended to have any limiting effect on the scope of any claim elements. In the figures, each identical or nearly identical component that is illustrated in various figures is represented by a like numeral. For purposes of clarity, not every component may be labeled in every figure. In the figures:

FIG. 36D shows experimental results of a swab design as described herein and shown in FIGS. 36A-36B versus a conventional flocked swab and cotton swab.

DETAILED DESCRIPTION

As discussed above, various embodiments relate to systems, methods and data structures used for representing 3D objects. In particular, 3D objects are represented by wireframe models which include one or more wires and/or other object types made up of wires.

Figure 1:
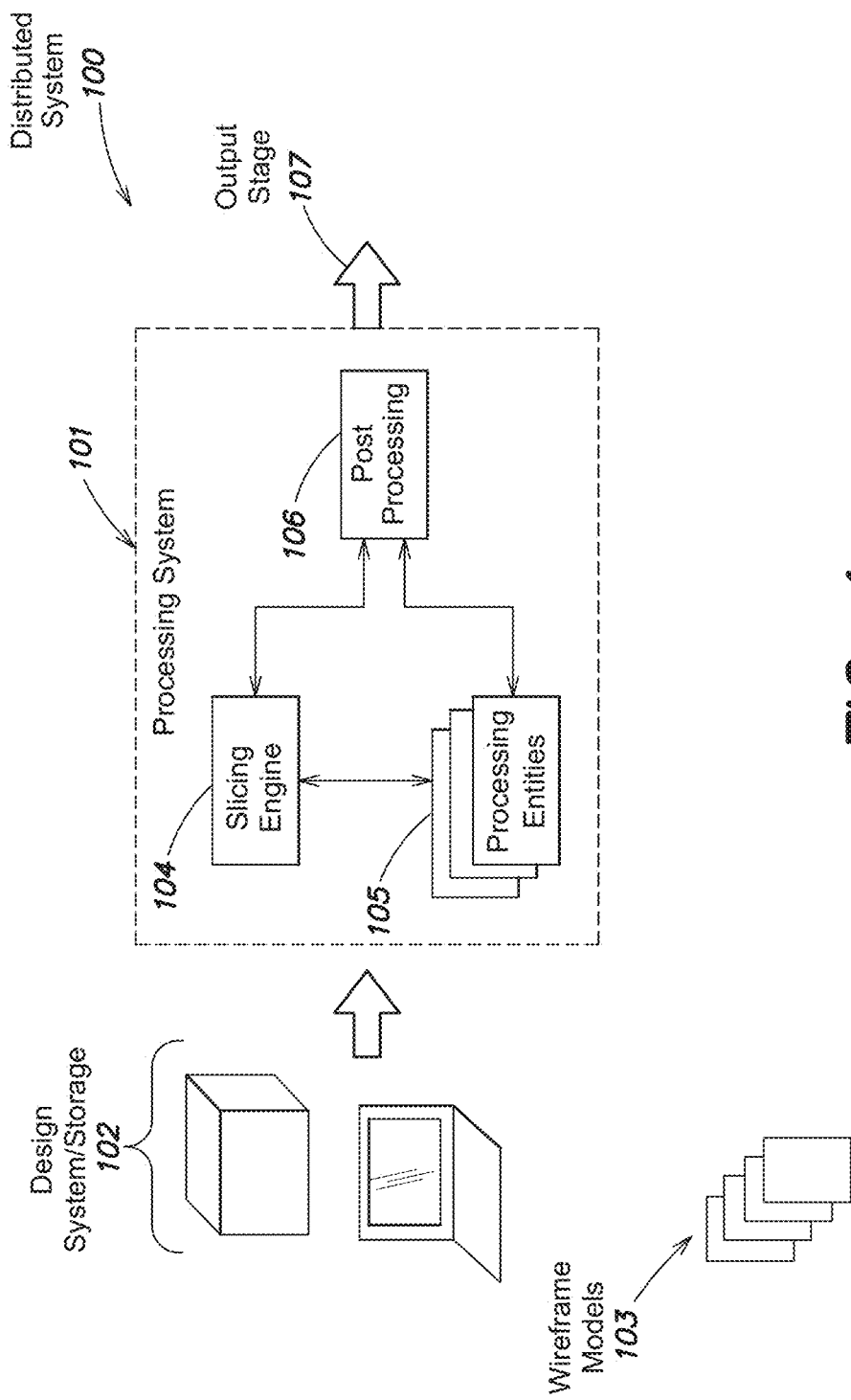
FIG. 1 shows a block diagram of a distributed computer system capable of processing wireframe models according to various embodiments.

FIG. 1 shows a block diagram of a distributed computer system 100 capable of processing wireframe models according to various embodiments. For example, one or more users may utilize a design system (e.g., system 102) or other system that is capable of processing and/or storing one or more wireframe models 103. Such a system may include, for example, a 3D object design software capable of defining one or more wireframe models.

In some aspects, a processing system 101 is provided that is capable of receiving wireframe models and processing them according to various embodiments. As discussed above, it may be beneficial to use wireframe models to reduce the weight of certain objects, rather than expressing them as solid elements. Because the system works with wireframe models, a file format is provided that is conducive for representing wires in a more easily processed manner. For instance, pressing system 101 may include a slicing engine 104 that is capable of slicing one or more wireframe models to determine a slice to be rendered and/or printed (e.g., such as by a 3D printer).

Further, in some embodiments, processing system 101 may include one or more processing entities 105 that are capable of processing different portions of a wireframe model in parallel. This is significant, as in traditional modeling type processing, parallel processing of a model is not possible. Processing system 101 may also include one or more postprocessing functions 106 that may be used to produce an output format which may be viewed, printed, or otherwise used by other processing entities in an output stage 107.

Figure 2:
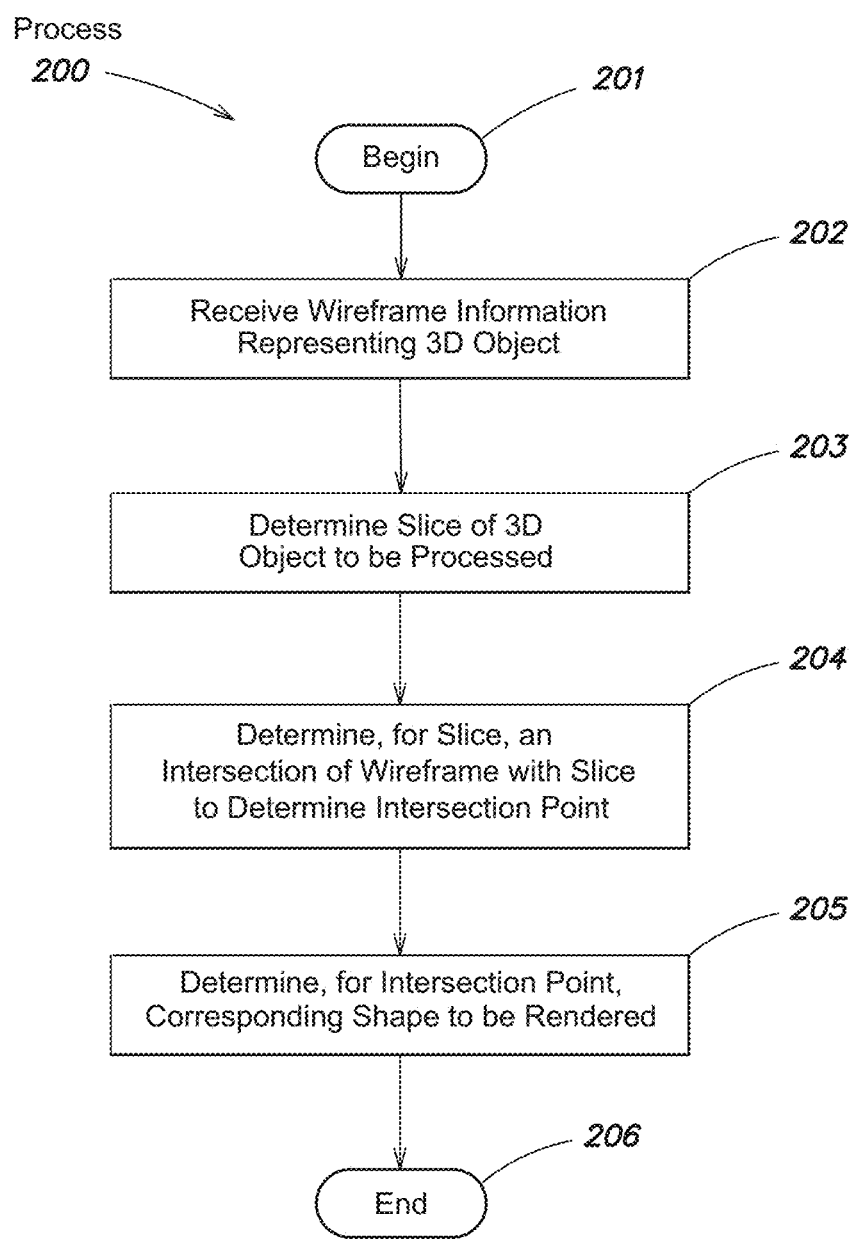
FIG. 2 shows a process for operating on a wireframe model information according to various embodiments.

As discussed above, one advantage of working with wireframe information is that elements of the wireframe object may be represented by lines that can be processed and in an easier way than traditional types of 3D modeling. FIG. 2 shows an example process 200 for operating on a wireframe model information according to various embodiments.

In particular, at block 201, process 200 begins. At block 202, the system receives wireframe information that represents a particular 3D object. At block 203, the system determines a slice of the 3D object to be processed. At block 204, the system determines, for each slice, and intersection of the wireframe with the slice to determine one or more intersection points. That is, given a particular cutting plane, one or more wireframe elements of the 3D model will intersect with the cutting plane defining a plurality of points to be rendered in that particular slice. At block 205, the system determines for each intersection point, a corresponding shape to be rendered. At block 206, process 200 ends.

As discussed above, a corresponding shape may be determined for each point that intersects with the cutting plane. The shape associated with the point may be rendered in the cutting place according to information stored in the wireframe model as well as a determination of the cutting angle in relation to the wire that passed through it. FIG. 5 shows how angle affects the shape of an intersection of a cutting plane to various conic sections.

Figure 3:
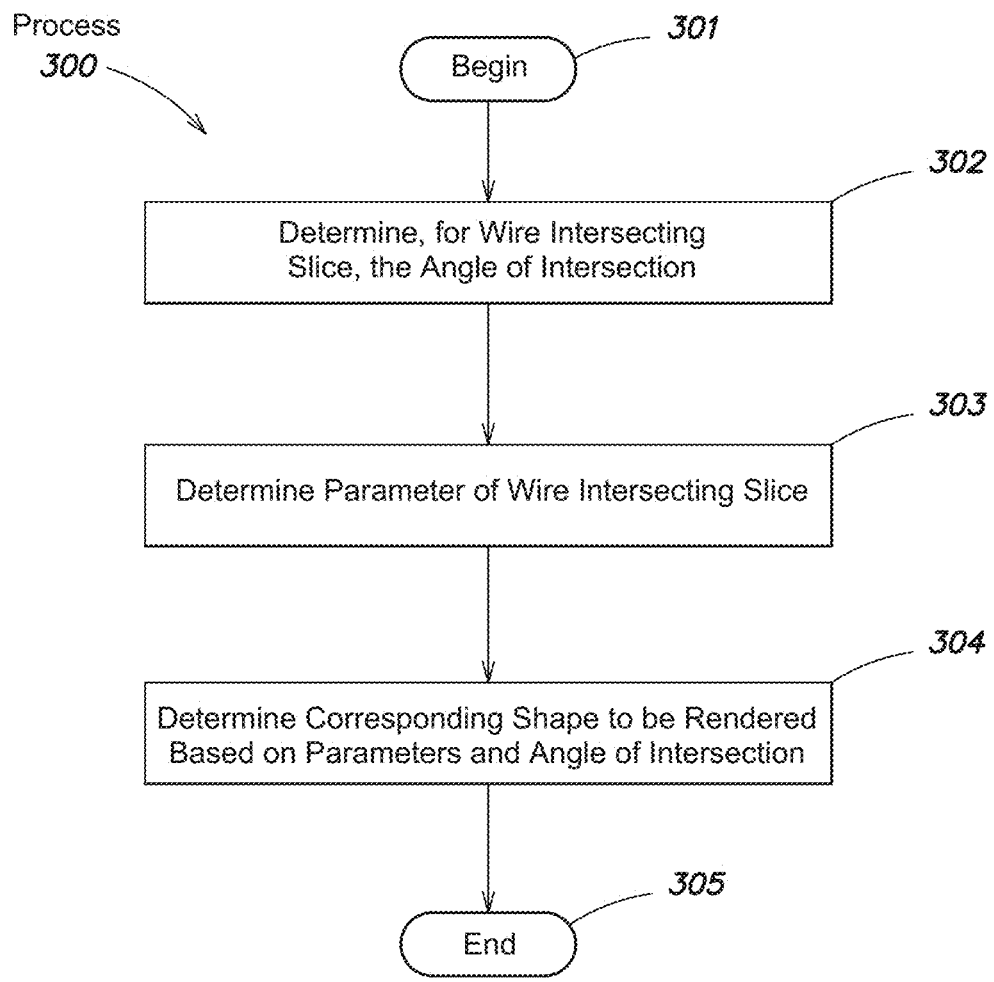
FIG. 3 shows a process for determining shapes based on an intersection of a cutting plane and a wire according to various embodiments.

FIG. 3 shows a process 300 for determining shapes based on an intersection of a cutting plane and a wire according to various embodiments. At block 301, process 300 begins. At block 302, the system determines, for a wire intersecting a particular slice, and angle of intersection between the wire and the slice. As shown in FIG. 5, the shape may change based on the angle of intersection of the cutting plane with the object. For a simple circular wire object, the angle of intersection may render a circle, a parabola, an ellipse, or a hyperbola. Further, the system may determine an associated parameter for that wire that intersects the slice. For example, within the wireframe model data file, several parameters may be used to describe a particular wire. For example, one or more parameters may control the thickness, shape, and/or twist of a wire object. At block 303. At block 304, the system determines a corresponding shape to be rendered for the point based on the parameters and/or the determined angle of intersection. This process may be repeated for any number of wire elements that intersect the cutting plane. For each iteration of the cutting plane, a 2D representation may be computed which can be rendered in an output (e.g., printed on a particular layer).

Figure 4:
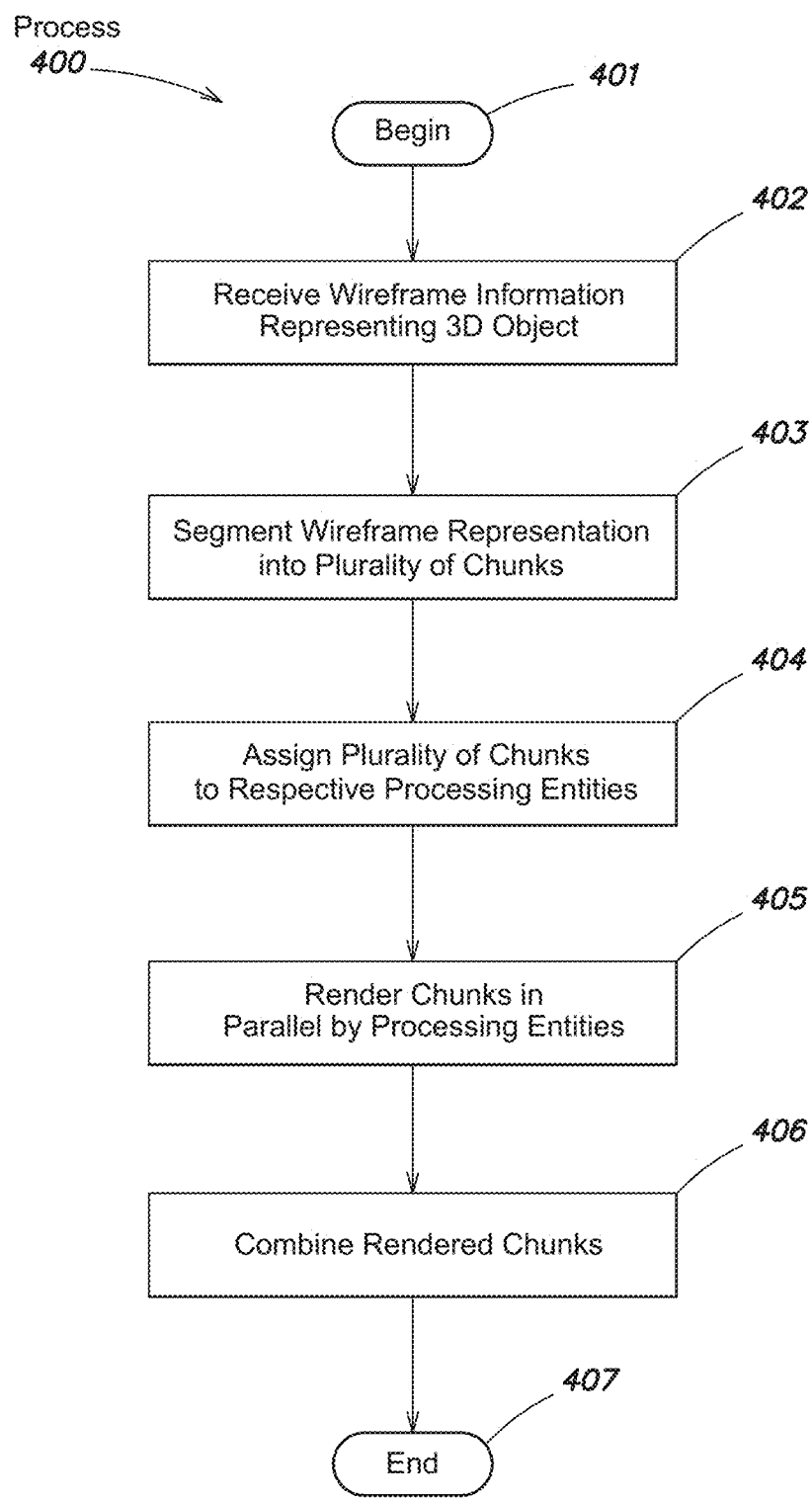
FIG. 4 shows a process for operating on 3D object representations in parallel by a number of processing entities.

Further, as discussed above, a 3D object represented by a wireframe representation may be processed more efficiently by multiple processing entities. FIG. 4 shows a process 400 for operating on 3D object representations in parallel by several processing entities.

At block 401, process 400 begins. At block 402, the system receives wireframe information that represents a 3D object. As discussed further below, the wireframe information may be stored and represented in a .MESO format. At block 403, the system segments the wireframe representation of the 3D object into a plurality of chunks. At block 404, the system assigns the plurality of chunks to respective processing entities. Each of the processing entities operates in parallel and renders their assigned chunk (e.g., in block 405). At block 406, the system may perform one or more post rendering operations, such as filtering, smoothing and/or combining of the rendered chunks. At block 407, process 400 ends.

As discussed above, computations for determining slice data can be simplified as the wireframe model may be interpreted as lines. In some embodiments, instead of parsing to a mesh model the .MESO data is "directly" interpreted as lines. In one implementation, for the 2D lines of the wireframe model positioned in 3D space, for each slice-layer, the intersections between lines of the model and the slice layer are calculated. This intersection point in 3D space can be translated into 2D coordinates of the slice data for each layer (x,y,z) in 3D space for layer #123 is on (u,v) of layer #123. In some implementations, for every intersection (for every layer) the shape of line intersection that has to be drawn onto the slice is then determined by the parameters of the .MESO line, such as diameter, profile shape, twist, and the intersection angle. This information is then used to calculate the corresponding appropriate parabola conic intersection (for circular meso line profile shape) as shown in FIG. 5A.

Figure 5A:
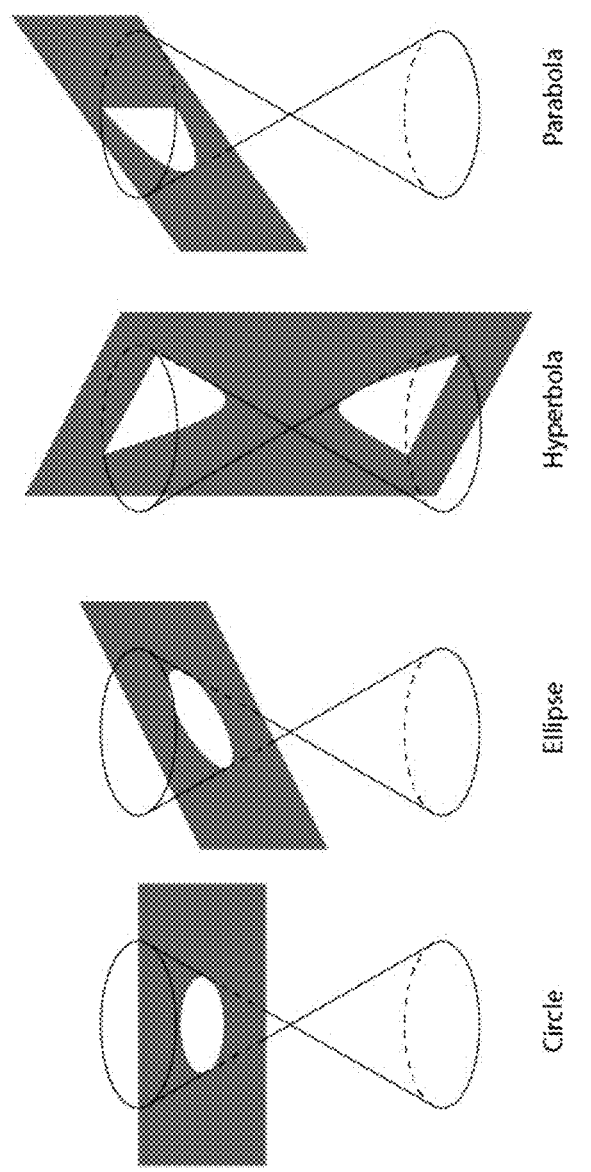
FIG. 5A shows an example method for representing wireframe information.

As shown, depending on the angle of intersection of the slice plane with the object, the shape may be any number of shapes as shown by way of example in FIG. 5A (e.g., parabola, circle, ellipse, hyperbola). The calculated conic intersection is then added to the slice data.

Because the wireframe model can be interpreted as lines, and for each slice, the intersections of the wireframe model may be calculated is a simple way, processing of the model may be operated on is in parallel. That is, for portions of the wireframe model, line-intersections and the conic intersections calculations can be computationally parallelized. This makes it potentially very scalable for large amounts of data in combination with the parallel slicing algorithms. Also, this slicing style is enabled by various embodiments of a .MESO file format, as line parameters such as profile shape, line diameter, etc. directly provided within the file format. The following are example implementations describing various embodiments, and it should be understood that various features may be used alone or in combination with other features described herein.

Example MESO Data Structure

In some embodiments, a data structure referred to herein as a .MESO (or .meso) data structure is provided that stores line information associated with the wireframe model. In some embodiments, the .MESO structure is an index-based data structure for mesh reconstruction and scan path generation for AM process. Although the .MESO structure is designed specifically for 3D printing mesostructure, with focus on fiber-like structures, this format can be applied to other areas. Such fiber structures could include but not limited to fibers, feather, lattice, woven structures and/or composite structures using various elements in combination. Although other index-base geometry formats have been used (for example .obj), .MESO data structures may provide support for operation and mesoscale geometries.

Design Considerations

In some embodiments, the .MESO format may exhibit one or more of the following design considerations:
  simplicity: abstract materials into wireframes and shell. adopt node graph to design geometries
  versatility: can design wide range of materials like fur, feather, lattices, woven or surface texture.
  fidelity: maintaining the fine feature of a design.
  scalability: can scale to design material that is meters long. can scale to design structures at nano scale.
  backward compatibility: with existing meshes.
  future compatibility: future features In some embodiments, some embodiments of a .meso format may provide a size reductions in the file size and/or a reduced processing load for printing. In some embodiments, a first size reduction mechanism is used. Firstly, in some embodiments, a .meso file format is an index-based data format, which is a feature that provides a significant reduction in file size. In one implementation of this format, a first part of the file contains 3D coordinates, the so-called nodes of the model. One benefit of this is to avoid redundant information to be stored multiple times. A second part of the file contains the data for connections between the previously defined nodes. In .meso, the volumes and meshes created reference coordinates previously defined as nodes. Through introduction of an index(node) based file formatting major parts of redundant information can be replaced by initial node definitions. For example, the vertex of a cube is defined as a node once and only its index referenced by meshes afterwards, instead of saving the node coordinates multiple times at different points in the file.

Figure 5B:
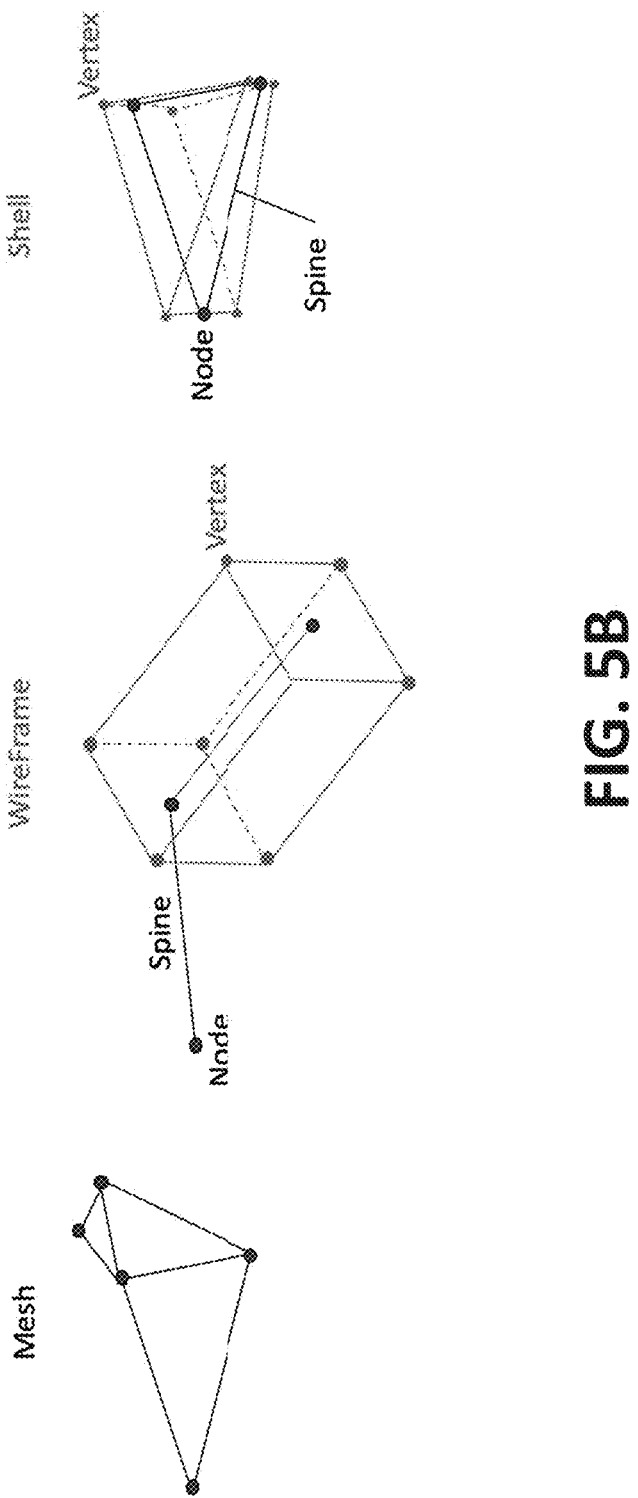
FIG. 5B shows various objects shapes that may be formed by intersecting a cutting plane with a 3D object.

Another file size reduction mechanism that may be used in the .meso format, is that the large amount of implicitly stored information in the data format itself. FIG. 5B shows how the file size reduction is accomplished. While standard 3D file formats in 3D printing explicitly store all information within the file, .meso stores higher abstractions of the data in the file. This means structures as wireframes (line shaped volumes) or shells (surface shaped volumes) are only described by their so-called spine. The reduction in file size becomes realized when comparing the line volume in the middle of the figure above. While standard file formats would store all vertices and meshes explicitly and separately and therefore 8 vertex points and 12 mesh triangles, the .meso format can save this structure with only 2 spine node coordinates and the profile and diameter information of the line. The reduction in file size is accomplished by the prior knowledge of the data format, that it is about to construct a wireframe line structure. Only the essential core information of the line is stored. The reconstruction to mesh or a compile process before production later on also contains sufficient parsing intelligence to deal with only the essential core information of the line. The file size reduction is achieved by higher encoding degree, which means more elaborate and intelligent parsing of the data.

There can be a tradeoff between the generality of a file format, and its usefulness for a specific purpose. In this tradeoff, the purpose of 3D printing at meso scale may be prioritized, which provides certainties in optimizing the exchange format. Further, there are some features of .meso file structure that are particularly useful in creating a compact file structure, including:

Self-Similarity

Elements such as fur and lattices are often made up of similar or identical modular units. These units could be repeated in a 2D, 3D, or fractal pattern, with small variations in transformation between units. Thus, the format can describe a series of geometry as a variation of its parent.

Shape-Blending

A capability of transforming between self-similar units also allows a degree of blending between discrete states of similar topology. This is a common feature in the natural world; from bone features between different species to feather proportions on a bird. This means that designers/manufacturers can create new geometries as a weighted blend of several discrete shapes of similar topology.

Distinct Features

At mesoscale, some features of the geometry became more prominent than others. This is particularly true to features that attribute to mechanical properties. Details of a certain size become less relevant as they approach the limit of printer resolution. This allows designers to put emphasis on dominant geometric parameters, such as cross-sectional profile, which could affect tactility of fur. Instead of a free-form shape, designers can describe mesostructures parametrically.

With such realization, instead of storing these geometries as volumetric meshes, a .MESO format according to some embodiments uses a simplified set of parametric descriptions to store the geometric properties of individual fiber. This technique allows any program using .MESO to reconstruct a large amount of geometries quickly with less information.

These parameters provide instruction for mesh re-construction. For example, the triangle of a fiber is reconstructed from a polyline curve with parameters of diameters, twisting angle, cross-sectional profile etc. This abstracted representation of geometries can strike a balance between scale and resolution. For example, a small sample of fur may consist of thousands/millions of individual hairs. On one hand, each hair should have characters and form that could be manipulated individually, on the other hand, they are variations of similar basic shapes. In some embodiments, a .MESO format takes advantage of the idiosyncrasy of fine fibers; This example format takes the assumption of some underlying organization, while allowing more expressive properties of the fur to be determined by the user.

Additional to reduced file size, some .MESO formats may offer several other benefits, compared to other mesh formats. Since each geometry is described parametrically, it is easy to modify these underlying parameters downstream, such as changing length or scaling diameter of each fiber. This is particularly useful in collaboration as it preserves the editability of a design. It also provides a simple and organized structure that allows users to easily extract useful information.

This has led to some characteristics of the file structure which are unique to some embodiments of an example .MESO data structure, including:

High Dependency Between Data

OBJ is a commonly used index-based file format. Unlike STL where each vertex of a triangle is stored as individual coordinates, in an OBJ file, vertices of triangles are retrieved from a shared list of points. This avoids redundancy in representing shared vertices and maintains mesh topology information, resulting in a compact and consistent mesh.

Figure 6:
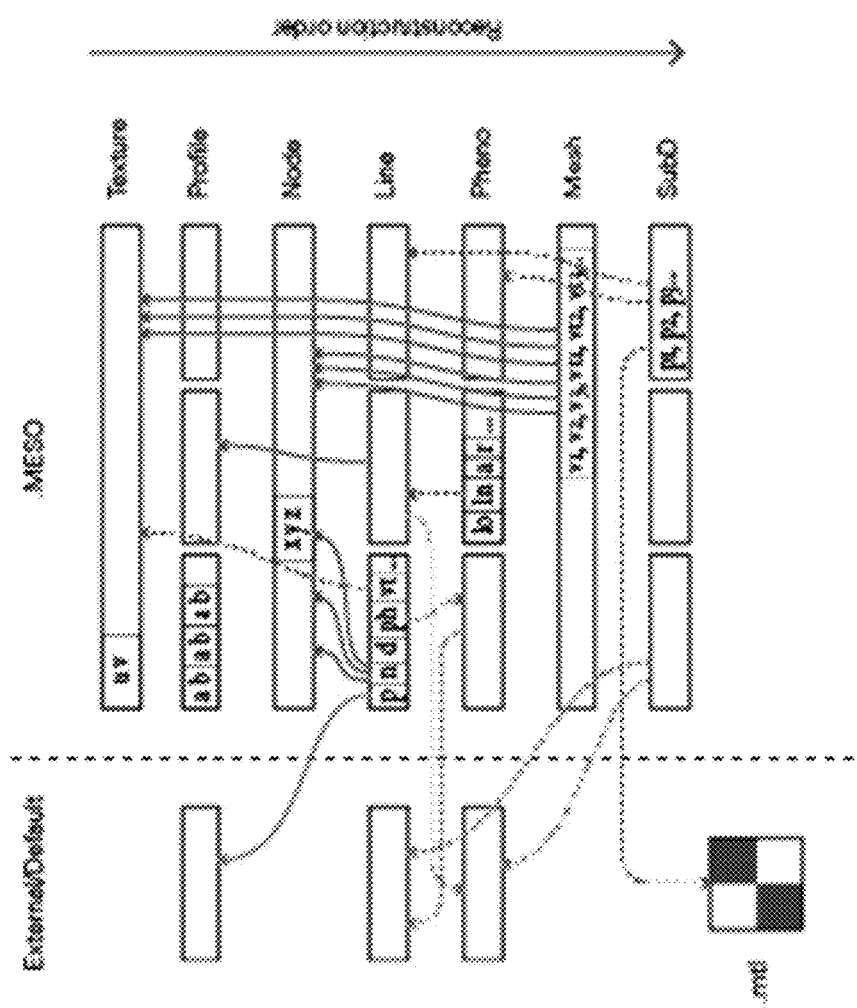
FIG. 6 shows an example .MESO format according to various embodiments.

In some embodiments, the .MESO format may use the same logic to reduce file size. With high self-similarities between geometries, in some implementations, the .MESO format may allow some geometries to be referenced in parametric functions. This provides an extra level of data efficiency as instances of detailed geometries are recorded only once and referenced many times. One example includes a reference of a child wireframe in a subD function, where one instance of wireframe and mesh face can create an arbitrary number of children through repetition. FIG. 6 shows an example .MESO format according to various embodiments.

Object Interpolation

Shape blending. To derive new shapes by interpolating several different shapes.

Data Structure Overview

A MESO file mainly contains two types of geometric information: 1) geometries and 2) parametric functions. Geometries include points (vertices), lines (wireframe) and surfaces (faces). These geometries are represented as connections among nodes, with additional information encoded at each node. parametric functions primary geometries which parametric functions will be applied upon.

Parametric functions are objects that contain parameters, which are instructions for specific functions during reconstructions and slicing. Parametric functions are independent objects in the data structure that could be referenced by geometries as a way to expand their own description. In most cases, these functions are used to generate children geometries from current ones.

In one embodiment, the .MESO format is built upon JSON schema. It contains the one or more of the following objects, alone or in combination with any other objects:

| | |
|---|---|
| Header | Description of file content |
| Node | A list of 3-D spatial coordinate |
| Wire | A list of nodes and their attributes |
| Shell | A list of Shell Faces and their attributes |
| Blended | A list of primary geometries and weights |
| Mesh | Legacy support for mesh geometries |
| Profiles | Parameters for thickening Wire |
| Branch | Parameters for creating children on Wires |
| Populate | Parameters for creating children on Shell Faces |
| Volumetric Mapping | Parameters for remapping 3D objects |

Header

The .MESO format may include a header that contains information for slicing software to process the file. This may include, for example, information identifying the material in which the object defined by the file is printed (e.g., materialID) and the type of machine that will print the object (e.g., machineID), and settings required to initiate the slicing process. It also contains information regarding ownership and date. In some embodiments, the file may include slicing settings that control actual geometry slicing.

Node

An array of 3D coordinates representing vertices of all primary geometry in the file. This array will be indexed as the file is imported.

| | |
|---|---|
| Coordinate [point3d] | X, Y, Z coordinates of the node |

Wire

Figure 7:
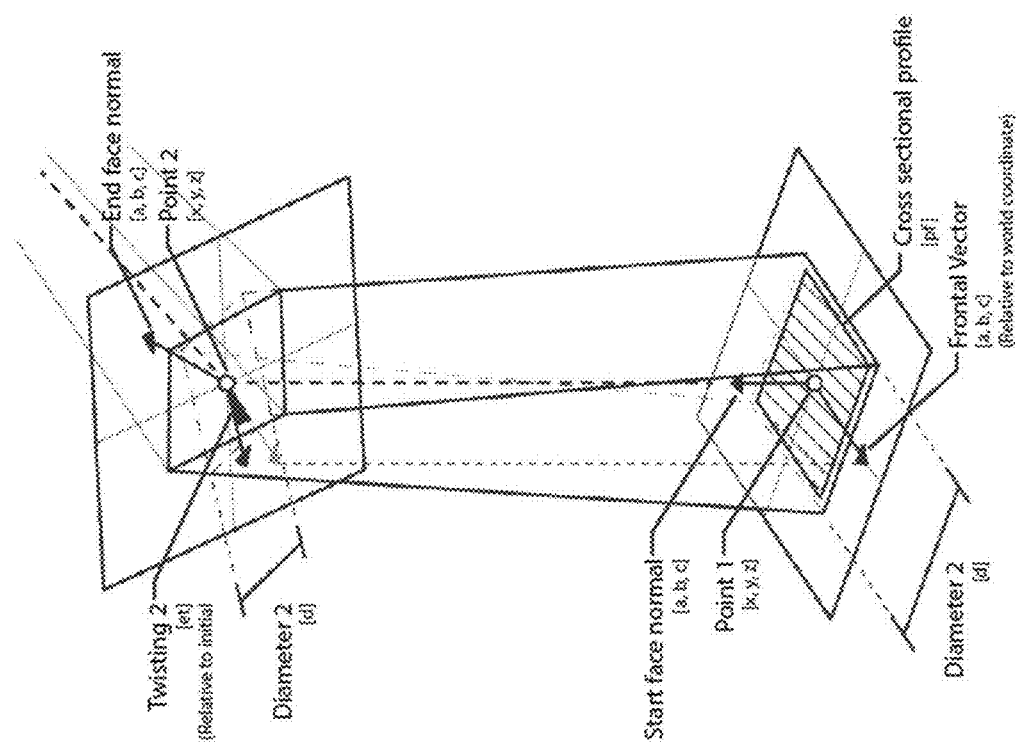
FIG. 7 shows an example wireframe representation of a simple wire according to various embodiments.

Each wire contains an array of nodes and attributes at each node, which enable a highly abstracted parametric representation hair-like or lattice structure. The collection of wireframe will be indexed. FIG. 7 shows an example wireframe representation of a simple wire according to various embodiments.

| Node [int]: | An array of indices pointing to the vertices of Fiber. This form the underlying central polyline spine of the fiber. |
|---|---|
| Diameter [double]: | An array of numbers representing diameter of fiber at each vertex. |
| Start Face Normal [Vector3d]: | Normal direction of start face. This creates a clipping plane with its origin at start point. |
| End Face Normal [Vector3d]: | Normal direction of end face. This creates a clipping plane with its origin at end point. |
| Frontal Vector [Vector3d]: | Frontal facing vector of profile in world coordinate and determine the orientation of the cross sectional profile. |
| Twisting [double]: | An array of numbers representing incremental rotation angle of profile. Each rotation is relative to the previous profile. i.e. set to 0 for a non-twisting straight hair. |
| Profile [string]: | Name of the Profile function. |
| Branching [string] | Names and weights of Branching functions. |
| Level [int] | Flag to indicate slicing level of this mesh face. See below. |

Mesh

Mesh provides compatibility to other file formats commonly used in additive manufacturing, like .STL. This should be a water-tight mesh.

Shell

Figure 8:
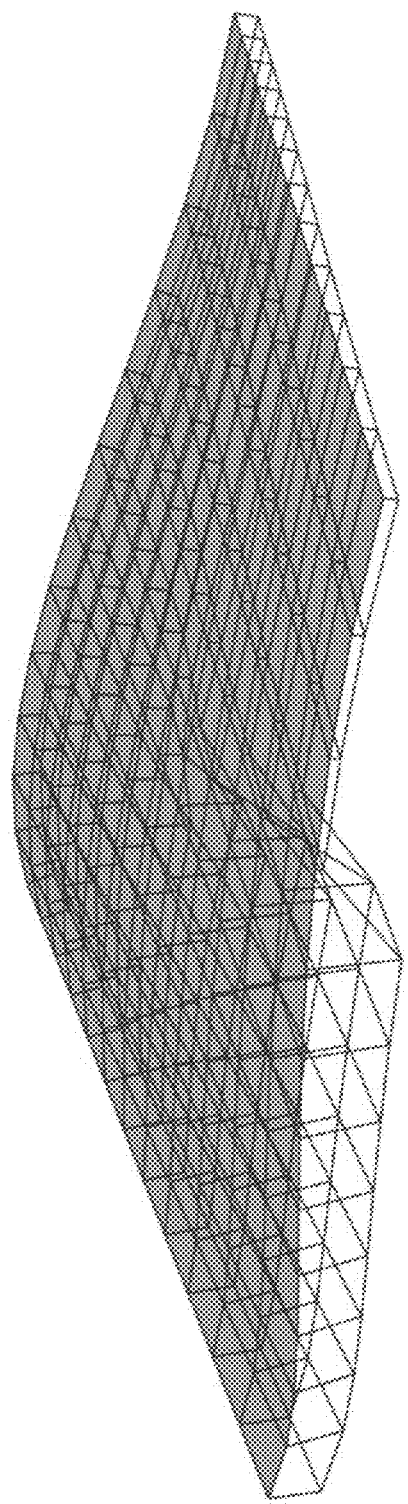
FIG. 8 shows an example shell representation which is capable of representing a surface.

Each Shell contains an array of Faces. Each Face contains between 3-4 instances of node information. Since thickness is assigned to each face, a Shell could be manifold or non-manifold, closed or opened. FIG. 8 shows an example shell representation which is capable of representing a surface.

| Node [int] | Indices of Shell Face nodes |
|---|---|
| Thickness [double] | Thickness of mesh face at each node. |
| Populate | Names of Populate functions. |
| Volumetric Mapping | Names of Volumetric Mapping functions. |
| Level [int] | Flag to indicate slicing level of this mesh face. See level description. |

Level Flag is used to indicate setting and behavior to be applied onto this geometry during slicing.

| 0 | Default |
|---|---|
| 1 | Exterior |
| 2 | Interior |
| 3 | Support |
| 4 | Mask |

Each volume holds a reference/index for the slicing settings used for the volume. Means: Save all x settings once, ID them, reference and safe ID only for each volume, will save file size and represents a flexible and adaptive formatting.

Further, a mask geometry may be used to create dark region(s). Discrete flags could be provided to limit slicing settings available to user.

Blended

Blended shapes are defined by weights of primary geometries. Its node location and attribute is a weighted average of those primary geometries it refers to.

| Node [int] | Index of node. Origin of Blended geometry. |
|---|---|
| Transform matrix | Transformation to be applied. |
| Parent [int] | Indices of parent geometries. |
| Weight [double] | Weight of parent geometries. |

Figure 9:
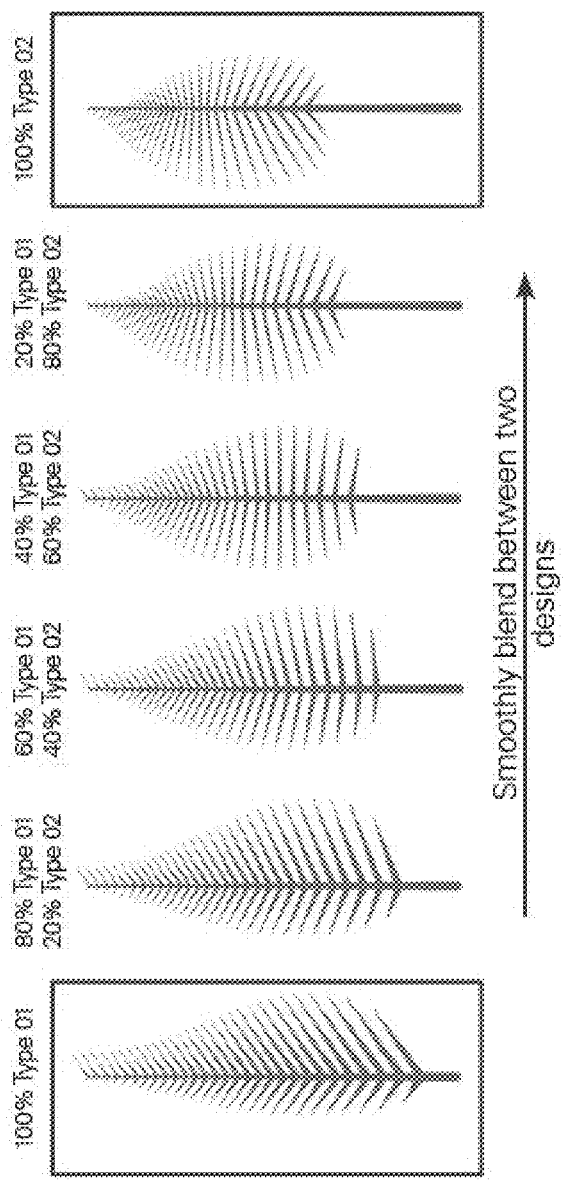
FIG. 9 shows a method for blending shapes using weighted averages.
Figure 10:
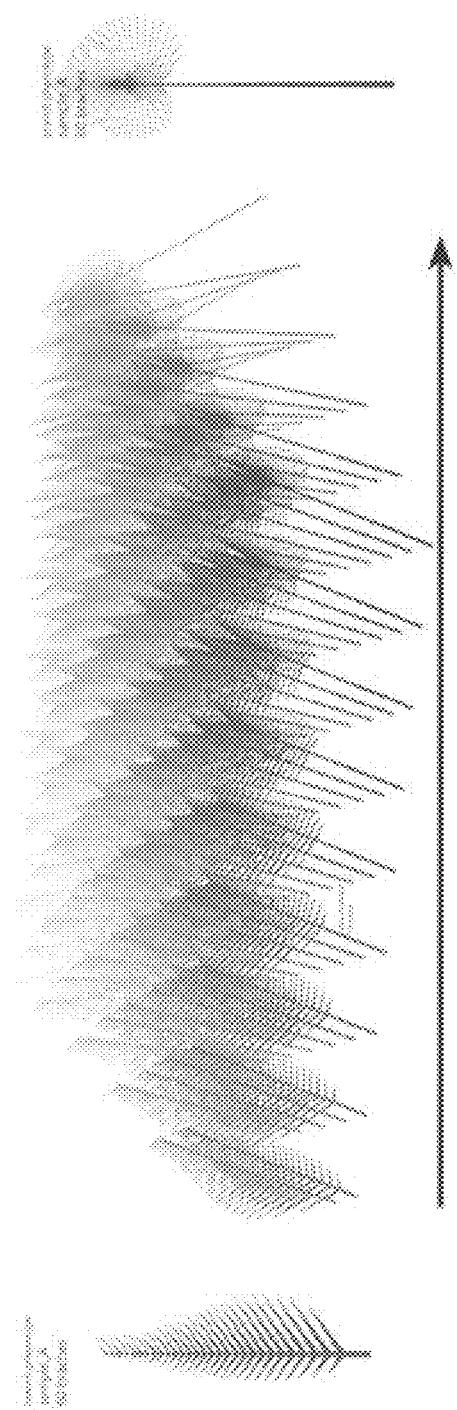
FIG. 10 shows a method for blending shapes along a surface.

FIG. 9 shows a method for blending shapes using weighted averages between two different types of designs. FIG. 10 shows a method for blending shapes along a surface, and the designs may be blended in multiple dimensions along the surface. It should be understood that any number of designs may be blended using a blended function.

Profiles

Profile contains a series of 2D vectors to expand/thicken each vertice of the wireframe. These vectors are transposed to the local orientation at each vertex, which align to curve normal and front vector.

| Profile Vertex [2D point] | Array of vectors representing profile outline. |
|---|---|
| Thickness [double] | Thickness for hollow tubes. Set to 0 to create solid. |

Branch

Figure 11:
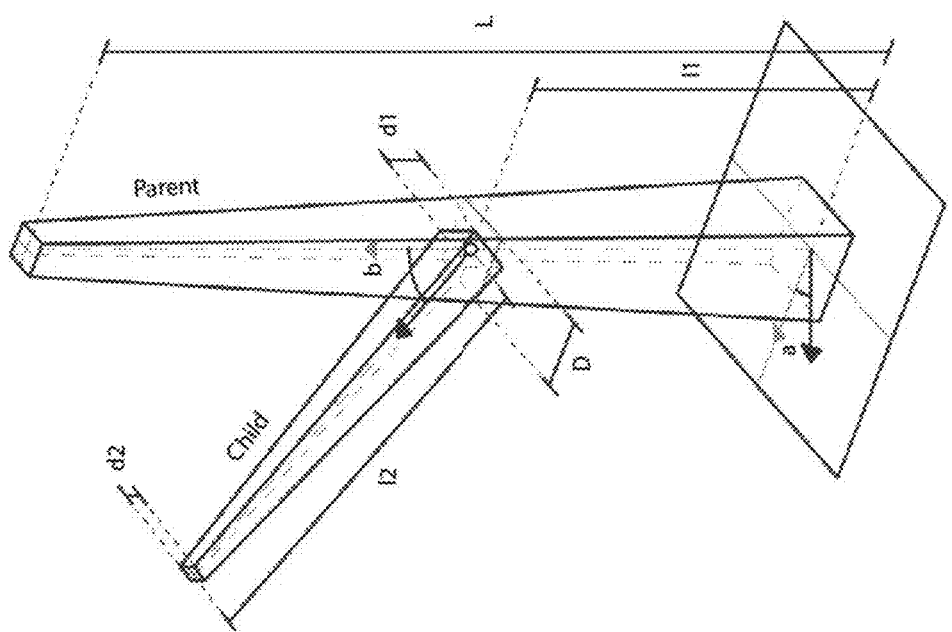
FIG. 11 shows an example wireframe representation of a wire having a branch or child wireframe that extends from a primary wire.

Branch contains parameters for placing a child wireframe onto a primary wire. FIG. 11 shows an example wireframe representation of a wire having a branch or child wireframe that extends from a primary wire.

| Location [double] | Array containing location on the wireframe to place the child. This will be a normalised value between 0 to 1. |
|---|---|
| Transformation matrix | Array of Transformation to be applied onto the child. |
| Child [int] | Array of index of child wireframe. If left empty, a simple line will be created with the transformation matrix. Child could not be identical to the parent to avoid recursive loop. |

Populate

Figure 12:
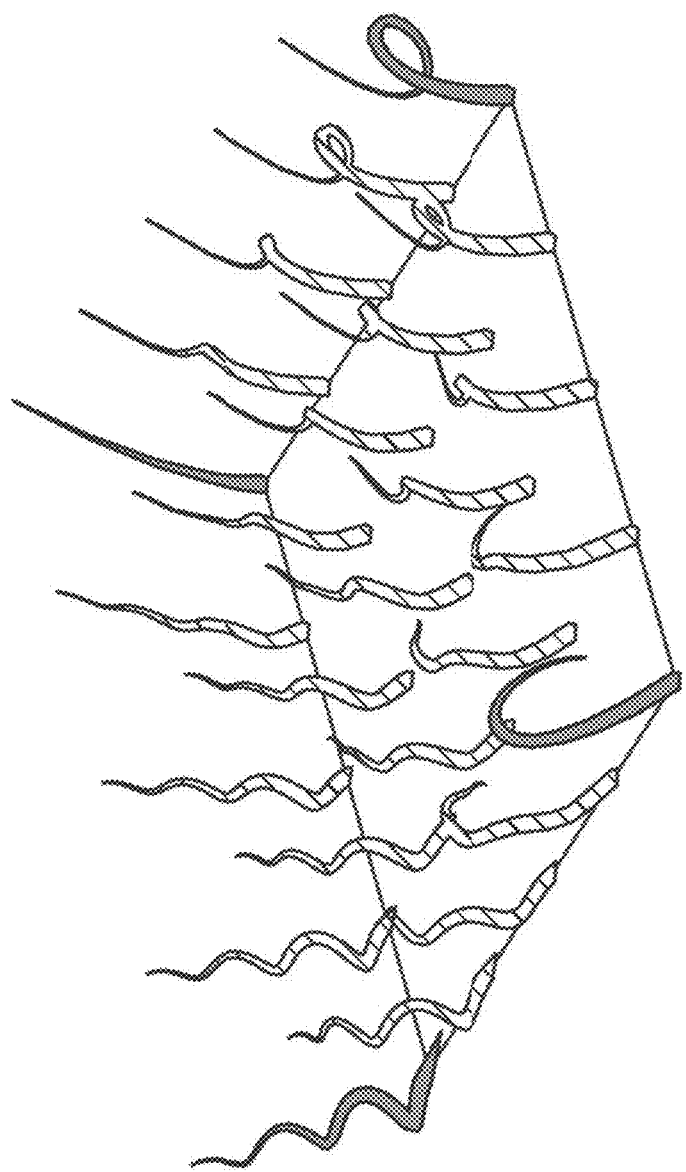
FIG. 12 shows a diagram of a number of wires populated on a surface.

Populate contains parameters for placing children onto a primary shell face (e.g., hair structures onto a surface). FIG. 12 shows a diagram of wires populated on a surface.

| Location [2D point] | Array containing UV location on the mesh face to place the child. This will be a normalised value between 0 to 1. |
|---|---|
| Transformation matrix | Transformations to be applied onto each child. |
| Child [int] | Indices of children on each vertex. If left empty, a simple line will be created with the transformation matrix. |

Volumetric Mapping

Box Mapping contains parameters to transform and distort primary geometry. Primary geometry will be remapped from a unit box at the origin to the uvw coordinate in target box.

| | |
|---|---|
| Node [int] | Indices of 8 Vertices representing 8 corners of the target box. |
| Child [int] | Indices of children to be remapped. |
| Subdivision | Subdivision count along edges of box |

Slicing

The term slicing in 3D printing is widely used to describe a procedure, at the end of which 3D printing production ready data is yielded. Therefore, the input of most slicing software is the virtual model data encoded in a certain data format, such as .stl, .obj or .meso. After passing through the slicing software, the data is converted into a manufacturing machine interpretable format to control the machine behavior, such as positioning of motor control units, laser pathways, projected images and so forth.

Because, in some embodiments, the manufacturing process that can be used is DLP printing, the slicing software may be focused mainly on the projected light sequences as a final result of the slicing in combination with other secondary printing settings such as platform movement speeds. As the taxonomy of slicing does not enclose the full-featured view of interdependencies between model data, slicing-, printing- and machine-settings in the overview of the entire production, designers tend to use the term compiling, as in compile to production data or compile to print.

The current state of the art for DLP, as well as most other commonly used slicing software in the 3D printing industry, is 3D mesh slicing. Justified by the prevalence of the stl formatting for 3D model data, slicing algorithms reconstruct other data formats back into stl-style meshes to be sliced via standard slicing algorithms. Although this procedure ensures high backwards compatibility, this could happen at the expense of efficiency and neglected tremendous potential for optimization. Especially with the objective to scale up 3D printing from prototyping to mass-production, factors such as computational effort in terms of time expense as well as a cost are important measures to boost productivity levels.

In addition to the already stated advantages of the .meso data format, the design language may be also created to be highly efficient when read, interpreted and compiled into printable production data. In some embodiments, there may be two (2) slicing engines as a core that may be used to compile .meso data into printable machine data:

Mesh reconstruction slicing engine
Direct wireframe slicing engine

.MESO Mesh Reconstruction Slicing

Figure 13:
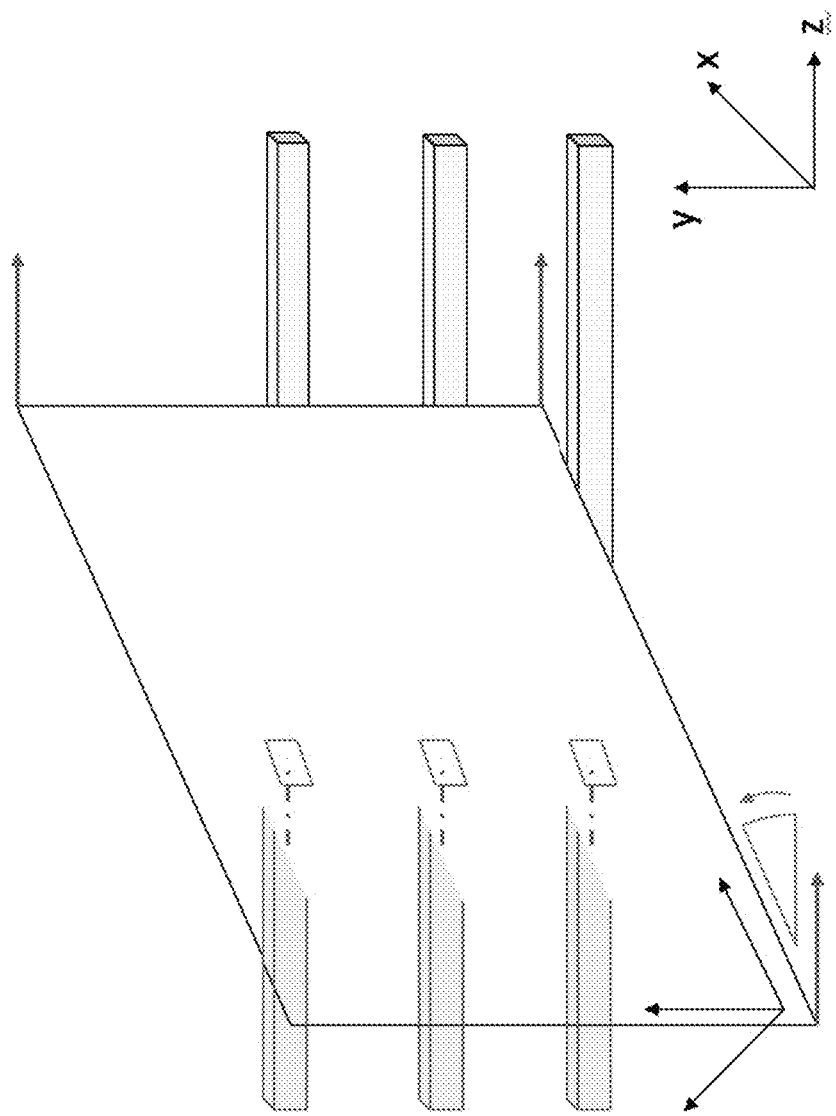
FIG. 13 shows an example process for slicing a 3D object according to various embodiments.

As shown in FIG. 13, an example process for slicing a 3D object according to various embodiments proceeds in a slicing plane that moves gradually in a parallel manner through the 3D object. The first slicing engine, mesh reconstruction slicing, is designed for backwards compatibility being able to process standard data formats such as .stl and .obj. Also, in some embodiments, the ability is provided to combine files with multiple different data formats, for example .stl in addition to .meso, and slice the combined model data. The virtual models are converted into two dimensional meshes, which when closed form the volumes to be sliced and printed. In some embodiments, an aspect of the algorithm is to create a cutting plane, which is continuously progressing through the model with a discrete step size incrementation. For DLP printing, this intersection plane may represent the projection surface of the light to be projected onto the resin. Therefore, intersection cuts between the cutting plane and the mesh enclosed volumes are computed for each plane incrementation step and saved as gray scaled bitmap image data.

In some embodiments of mesh slicing, a GPU slicing algorithm is chosen, based on mesh face culling operations. The comprised volumes are detected by evaluating the amount of triangle meshes facing in and out of the active field of view of the incrementation step. For this slicing technique to run on GPU, one can reconstruct the entire model with 2D meshes with a determined facing direction. The two-dimensional intersection cuts of plane and model volumes are saved as image data in bitmap format. Every intersection cut, also called layer or slice, is later projected onto the resin.

A GPU slicing algorithm may be, for example, a mesh reconstruction with mesh face culling slicing algorithm. The algorithm determines whether the current slicing layer is inside or outside of a volume by incrementing and decrementing the amount of inward and outward facing mesh faces. For example, for a simple cube: Outside of the cube in front view, both cube faces face the current view layer. The total amount of inward facing faces is 2. For even facing number increments, the algorithm determines to be outside of a volume for this area. If the current view layer is placed inside of the cube and therefore cutting it, the amount of inward facing faces is 1, which is an odd number, and therefore it is evaluated to be inside of a volume. The corresponding pixels in the slice will be evaluated to be filled.

A direct line slicing algorithm may be used, for example, that does not reconstruct the actual mesh of the .meso file before slicing it. The GPU slicing algorithm is used to create line projection cuts on the slices directly. A mesh reconstruction generates all implicit information from the explicit information in the .meso as a mesh from the .meso. This data is used for mesh reconstruction face culling slicing. For direct line slicing, no mesh reconstruction of all implicit information is done before. The decoding of this information is done "just-in-time" while slicing exactly this wireframe line, when it intersects with the current slicing layer. In case of an intersection of wireframe line and slicing layer, the explicit wireframe line information, such as diameter, twisting angle etc., is used to evaluate the projection cut of this line to be saved as pixels on the slice.

.meso Direct wireframe slicing

Figure 14:
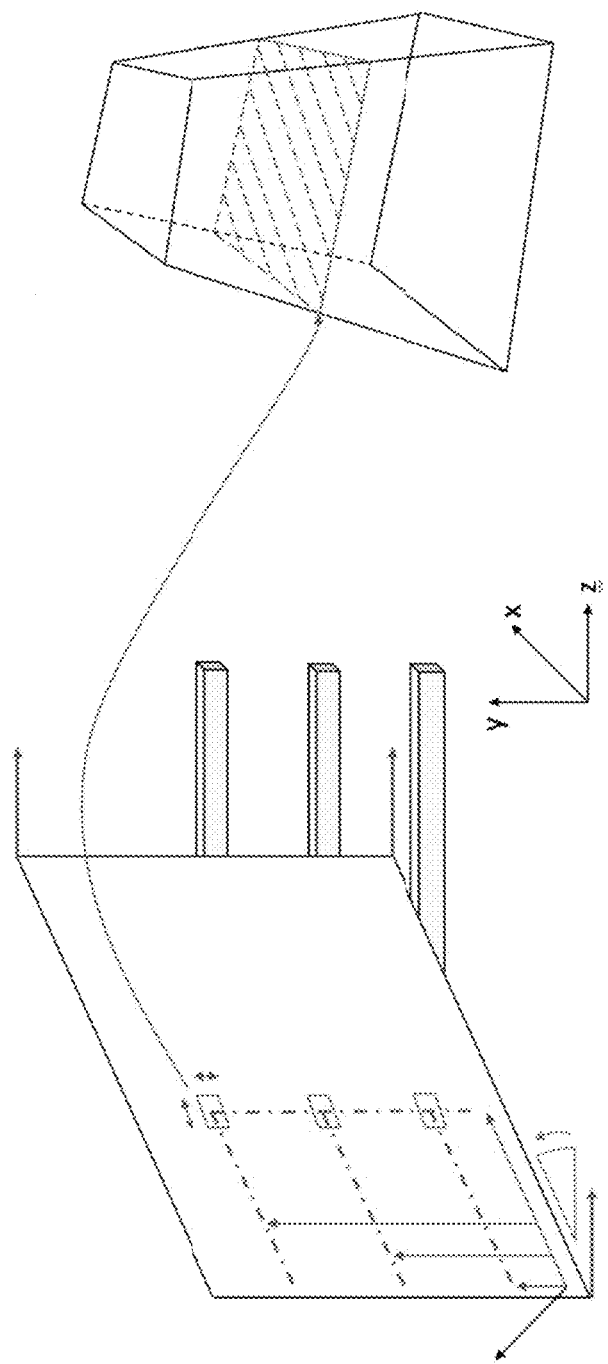
FIG. 14 shows an example process for slicing a wireframe representation according to various embodiments.

The second slicing engine, direct wireframe slicing, is optimized for the internal .meso data format. FIG. 14 shows an example process for slicing a wireframe representation according to various embodiments. By taking into account that the .meso data format does not incorporate meshes and therefore the surfaces, but is based on a more abstract description of entire bodies, as of yet specifically with a focus on line-based structures, it is possible to bypass the mesh reconstruction and mesh slicing technique. The direct line slicing engine uses the conceptional representation of the smallest building blocks within the .meso designed structures, the one-dimensional mathematical concept of a line.

Coming from the linear algebra concepts of the arrangement of one-dimensional lines in three-dimensional space, the engine utilizes this vector space to calculate all line intersections with a cutting plane via linear equations. Again, this cutting plane can be moved in discrete steps, layer by layer, through the model space as shown in FIG. 14. For each increment all intersections between the 2D plane and all 1D lines are calculated, resulting in intersection points (temporarily). The orientation of those intersection points in 3D space can be described in the local reference coordinate system of the slicing cutting plane (indicated in red).

The .meso data format, as described above, contains information about each line, such as diameter, profile twisting angle and so forth, which is then utilized at this point (Compare: Used before slicing to reconstruct model into meshes for mesh reconstruction slicing). With the information of intersection points, start- and endpoints of the lines, and the additional information of profile, diameter etc., the projected 2D plane can be calculated, which may be necessary to create the desired 3D volume output. For example, the mathematical description of projections of cylindrical circle-profile lines can be derived from conic section cuts as discussed above.

In combination with the applicable parallel slicing (e.g., a model reduce algorithm), this can boost computational efficiency of the slicing especially for large model sizes. The direct line slicing of .meso files, enabled by the bypassing of global model mesh reconstruction, allows to run slicing algorithms to local sub partitions of .meso files and in combination with the just-in-time involvement of line parameters in the last algorithm step, this algorithm is arbitrarily scalable and parallelizable for distributed slicing.

Parallel Slicing/Distributed Model Algorithms/Model Reduce

Figure 15:
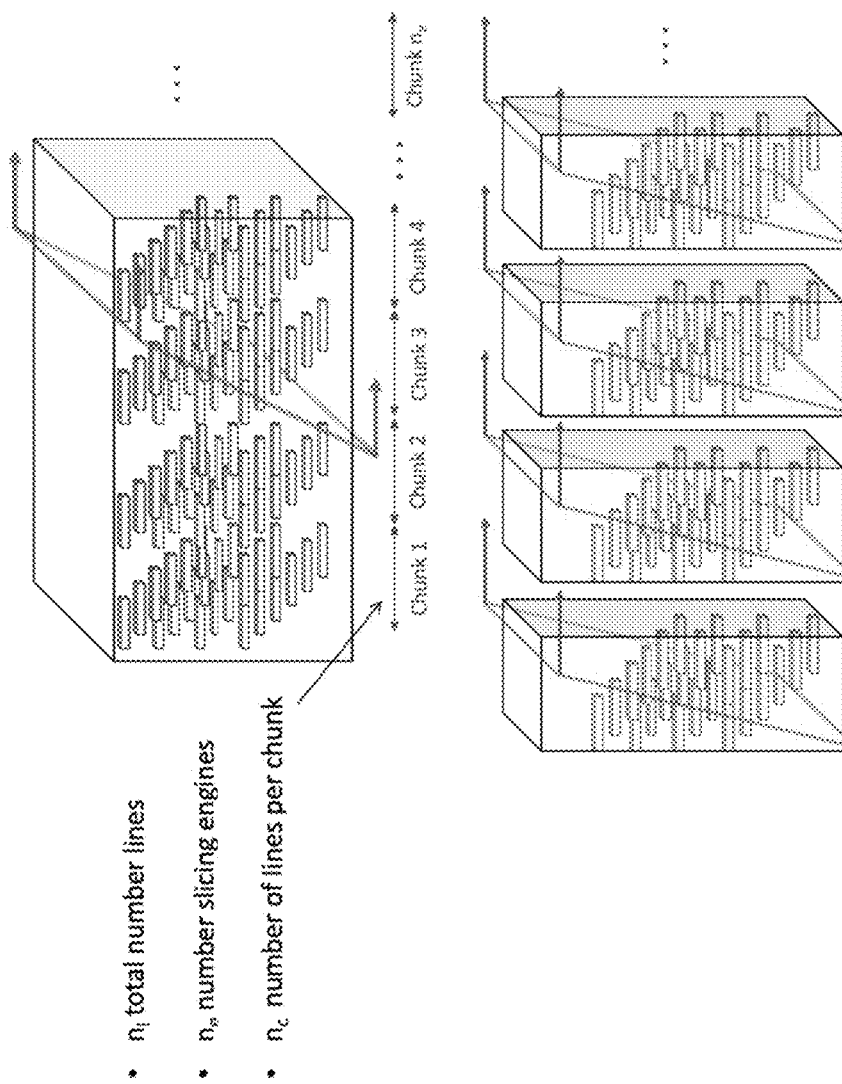
FIG. 15 shows an example process for processing portions of a 3D model in parallel according to various embodiments.

In some embodiments, a model reduce algorithm for parallel slicing is provided that originates from the possibilities opened by the direct line slicing approach to parallelize slicing algorithms within a single model. Standard data formats follow a rather indirect approach to formulate volumes by defining meshes that might create volumes in case they are fully closed. This not only leaves plenty of room for common and very frequent mistakes such as not closed meshes and surfaces resulting in glitches and non-fail-safe behavior of the format with global errors, but also fails to pass on information about positioning, start points and endpoints of volumes and their local extent. FIG. 15 shows an example process for processing portions of a 3D model in parallel according to various embodiments.

In some embodiments a .meso format provides start points and endpoints of volumes, which is beneficial for processing to distribute models into local sub models and to distribute computational tasks into multiple smaller ones. The model reduce algorithm provided here can be categorized as a so-called divide and conquer algorithm. In some embodiments, the inventors have realized that a big data algorithm referred to as "map reduce" may be used to deal with big 3D data models in a more efficient manner.

The core concept of the model reduce algorithm is to partition the model, for standard slicing oversized, into several smaller ones, which can be dealt with in a distributed computer cluster architecture (or also just multiple threads or other processing entities) in parallel. Key to the decomposition of the model data is the spatial dependency of 3D data, which can be accessed in .meso due to the included line start points and endpoints. Unfortunately, this information is not supplied in standard formats, such as .stl or .obj.

Based on the spatial positioning of all lines, the entire dataset can be sorted. For example, for parallel slicing the sorting criterion is the slicing direction (z-axis). According to this rank order, the model can be separated into multiple locally fully independent sub-models, also called chunks. A rule of thumb for accelerated slicing might be to separate the model into a number of chunks equal to the amount of processing cores available in the cluster (and/or other processing entities like virtual processors, threads, or other processing entity). In the rather common case of the model not having clear/empty areas to separate the model, for example lines starting at the global models start and ending at the global models end, there are several ways to deal with it. One approach is to copy and transfer those lines into every traversed chunk. Another approach is to automatically restructure the dataset by separating overly large/long lines into multiple smaller ones.

In some embodiments, each chunk is a fully self-sufficient meso sub-model with all properties of the "parent" meso model. Thus, each chunk can be sliced individually as its own instance. From one large .meso model that is too large to efficiently slice as one for a single processing entity (e.g., GPU memory), the system may distribute the model into multiple meso sub-models (which sizes are efficient to slice for a processing entity). With the information of the arrangement and structure of the sub-models within the parent .meso model, the resulting slices for all sub-models can be combined/fused/superimposed to the overall slicing result of the parent meso model.

By using the .meso file format data, which contains individual and discrete volume objects (see meso volume classes) plus a node based system, it is possible to process large models in an easy efficient and fast way. In contrast, a conventional single mesh data file cannot not be distributed into sub-models and spatial chunks in such a quick way.

In one implementation, the spatial sorting for sub-models/chunks can be done with an algorithm such as: Define chunks in meso parent model volume space (for example equidistant in slice direction, such for example in y-dimension four same length chunks). Then, all nodes of the meso parent model are assigned/labelled internally to which chunk they belong, so in which chunk they are spatially located (or in doubt they are labelled for two chunks). For each chunk, a meso sub-model is created in which all meso objects/lines are written, that have nodes within this chunk (additionally in-reaching objects/lines, which have nodes located within a close distance to that chunk and their volume radius can potentially reach into said chunk). The nodes for all sub-models can be left untouched as are in the parent model. Now all sub-models can be sent out fully independently to virtually and/or physically separated processing entities (e.g., slicing engine programs/routines executing workstations, GPUs, cloud instances etc.). After the submodels are fully processed, the resulting slices data is merged into the global parent meso model volume space (e.g., simply appended in terms of equidistant chunking along slicing direction).

The model reduce algorithm can be applied to parallelize 3D slicing algorithms, but is not restricted or limited to this. Other applications in 3D modelling, such as nearest neighbor searches or filtering operations can benefit from distributed and parallel computing as well.

Meso scale printing should be approached as an interdisciplinary approach, and the quality of the print is dependent on various interdependent factors. Some of them are related to the computational slicing. Other fields such as machine settings, machine process control, resin material properties etc. not only crucially affect the print quality but also interact with one another and also the slicing. Therefore, different slicing intensity filters for example can have various results for different resins or machine setups regarding print quality and resulting properties. This interdisciplinary view of the entire process from virtual model to finished product as compile. In some cases, many aspects of this compile process are done manually by hand and empirical human experience to tune settings and parameters for the optimal print.

DLP Printing Light Intensity Filtering

Figure 16B:
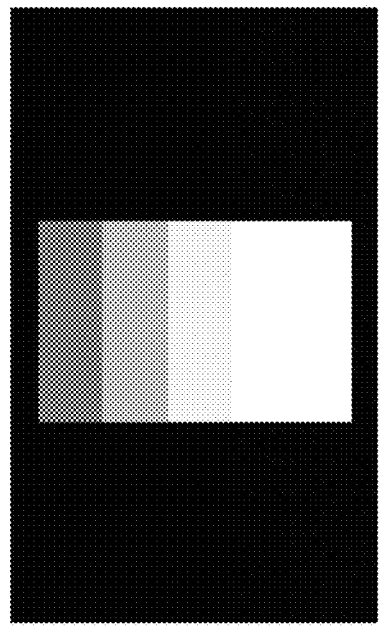
FIGS. 16A-16B show various embodiments of image postprocessing.
Figure 16B:
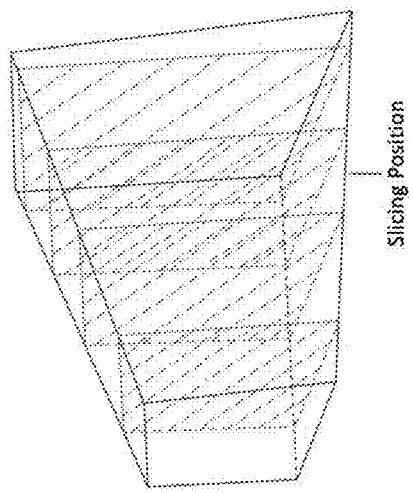
Figure 16A:
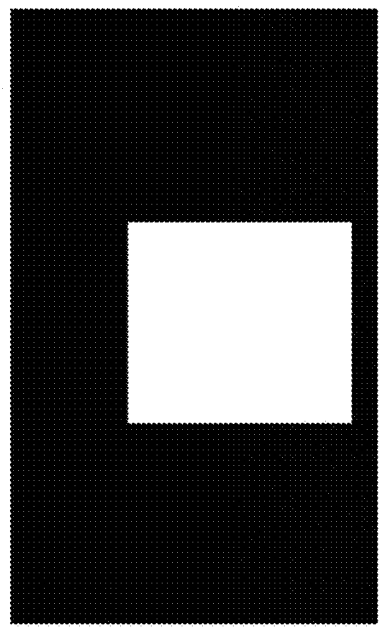
Figure 16A:
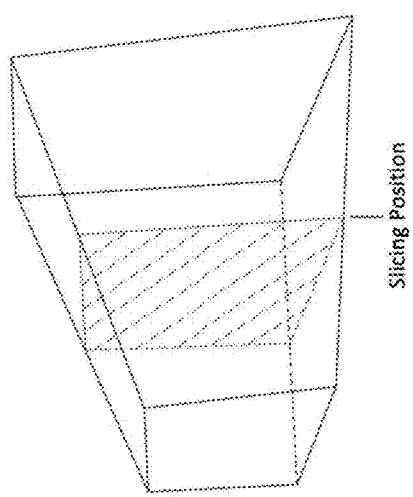

The compile process, in some embodiments, can also include an image/bitmap data post-processing after each slicing step. To receive a smoother transition between individual layers a depth subsampling is applied through not only determining a single intersection cut between slicing plane and 3D model, but slicing the model multiple times (parameterized by the desired subsampling degree) (e.g., in equidistant steps) and to subsequently average the pixel intensities. Depth subsampling is illustrated in FIGS. 16A-16B which show various embodiments of image postprocessing using depth subsampling or not.

This results in less sharp and distinct edges caused by the slicing and layer-wise production of the print. Undesirable staircase approximations of inclines and slopes in the model geometry are prevented by applying the depth subsampling method described here. The different gray scaled pixel intensities of the projection produce a generally smoother surface of the prints.

In addition to depth subsampling, anti-aliasing within the slicing plane is performed by Multisample anti-aliasing (MSAA). The MSAA reduces pixel intensity gradients for the already subsampled slice and smooths out too sharp corners and edges in the image data. Especially for slicing and printing angles deviating from standard 90-degree, bottom-up and top-down, subsampling in combination with multisampling enables to maintain the ability to print at highest pixel resolution.

Figure 17A:
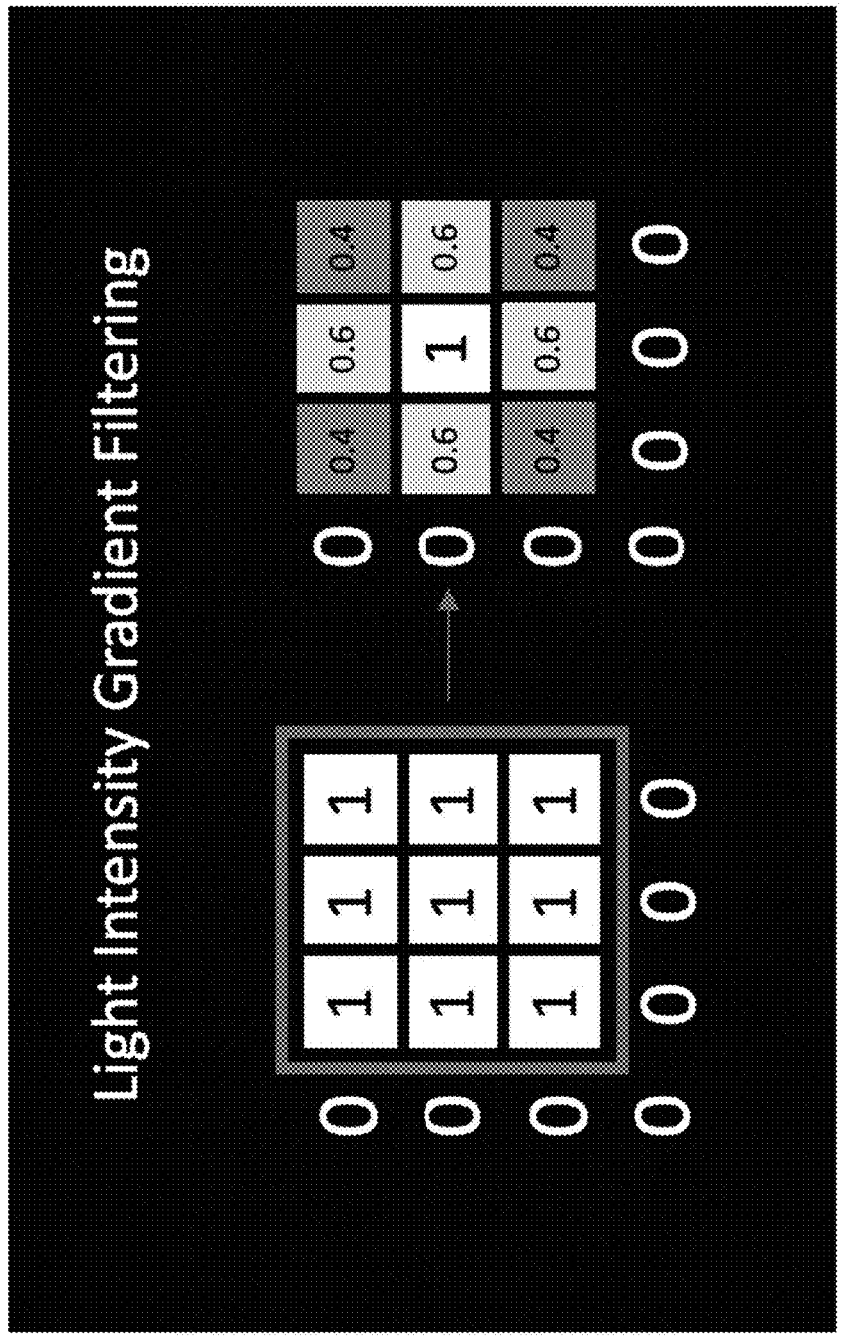
FIG. 17A shows an example light intensity gradient filtering operation according to various embodiments.

Afterwards, a light intensity fragment filter is applied to optimize the quality of the print by adjusting the projected light intensity for an optimal resin curing. For example, this can include evaluating the light refraction and light absorption during the curing process and optimization regarding used resin and desired geometry. The first option for this post-processing step is the standard default setting, which will not change any pixel values and pass-through the pixel data after sub- and multisample slicing. The two other filter categories, gradient and hollow gradient filtering, are provided in square as well as radial alternative. Those filters apply customizable kernels to the gray-scaled bitmap data after slicing. For example, the square gradient intensity filter for a single active pixel (e.g. a small hair) would create the result shown in FIG. 17A.

Figure 17B:
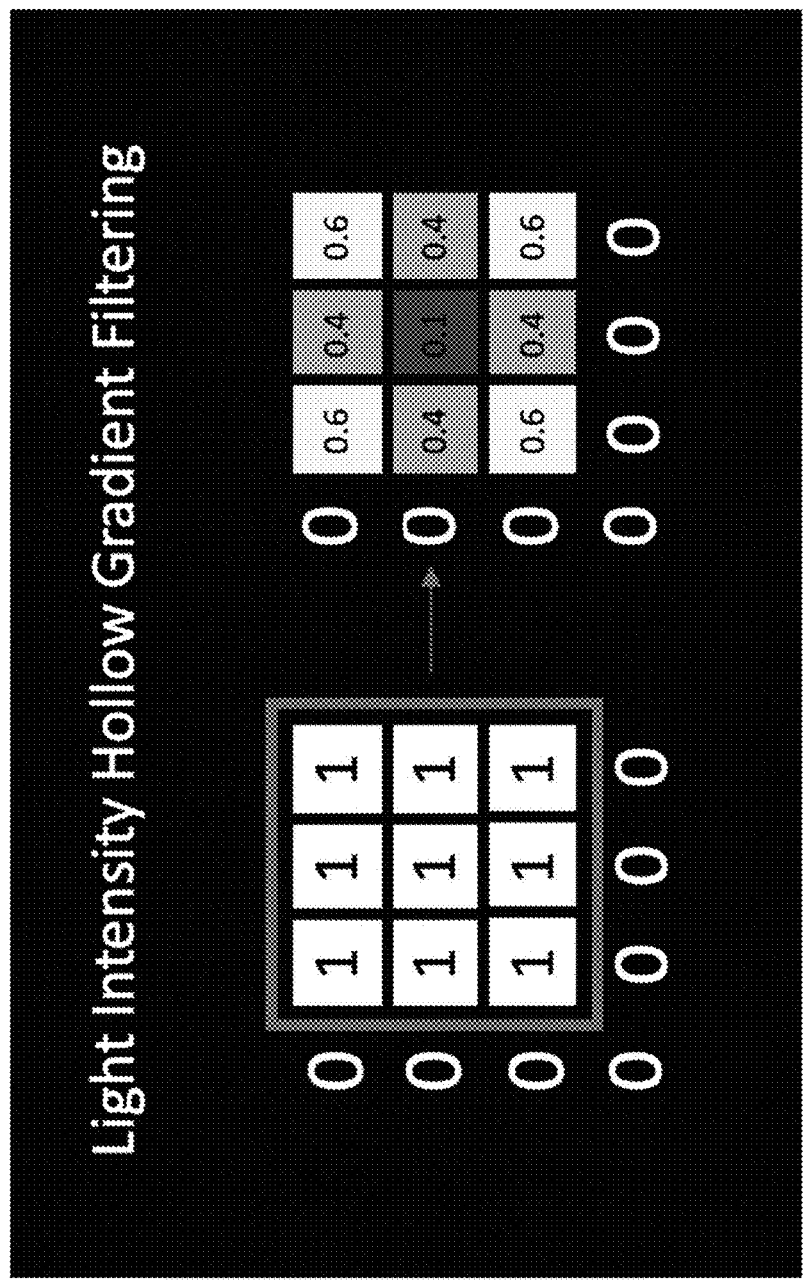
FIG. 17B shows an example light intensity hollow gradient filtering operation according to various embodiments.

The gradient filter is applied by calculating the kernel for active pixels (not 0) pixels for the entire image. In addition to the filter range given in a number of pixels (half sidelength for square and radius for radial filters), cutoff-brightness and minimal-brightness can be defined for the filters. In the example shown in FIG. 17B for hollow gradient square kernel filtering, the minimal brightness is set to 0.1, so that the core of the structure is not 0, but 0.1.

The minimal brightness is activated, in case the filter is about to set a pixel value below this threshold. The threshold value of minimal brightness is set instead then. Also, cutoff-brightness as the opposite can be applied with the effect of setting all pixel values below a defined threshold value of the cutoff-brightness to 0.

Figure 18A:
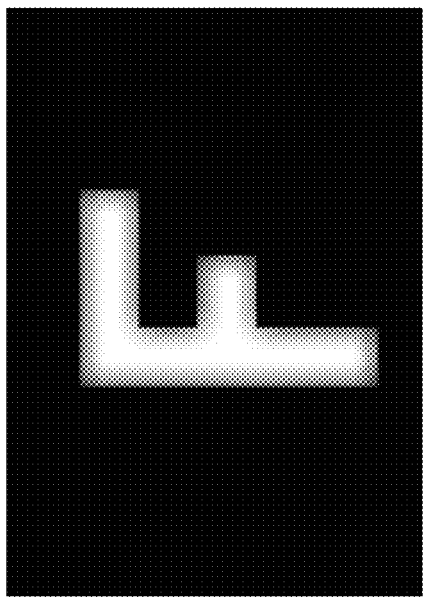
FIG. 18A shows an example starting slice of a 3D object.
Figure 18B:
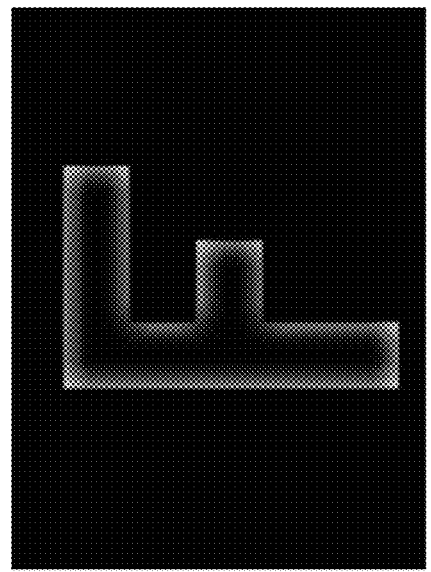
FIG. 18B shows the example starting slice of FIG. 18A with the light intensity hollow gradient filtering applied.

FIG. 18A shows an example smoothing function of corners of a 3D object, and FIG. 18B shows the example with the light intensity hollow gradient filtering applied. In FIG. 18A, an example for a gradient intensity filter with radial kernel and filter range of 25 is given to illustrate the resulting effects of smoothed out intensity corners. Also, FIG. 18B shows a hollow gradient filtering applied with radial kernel and 25 pixel range. This can especially be useful to print hollow structures or in combination with higher minimum brightness values applied to print larger solid and plane like structures without complications. The fine-tuning of intensity filter optimization for certain resins and model geometries can be a difficult task, due to the large number of involved factors. An automation of this process is conceivable with higher-level user input, such as tailor-made material properties.

Figure 19:
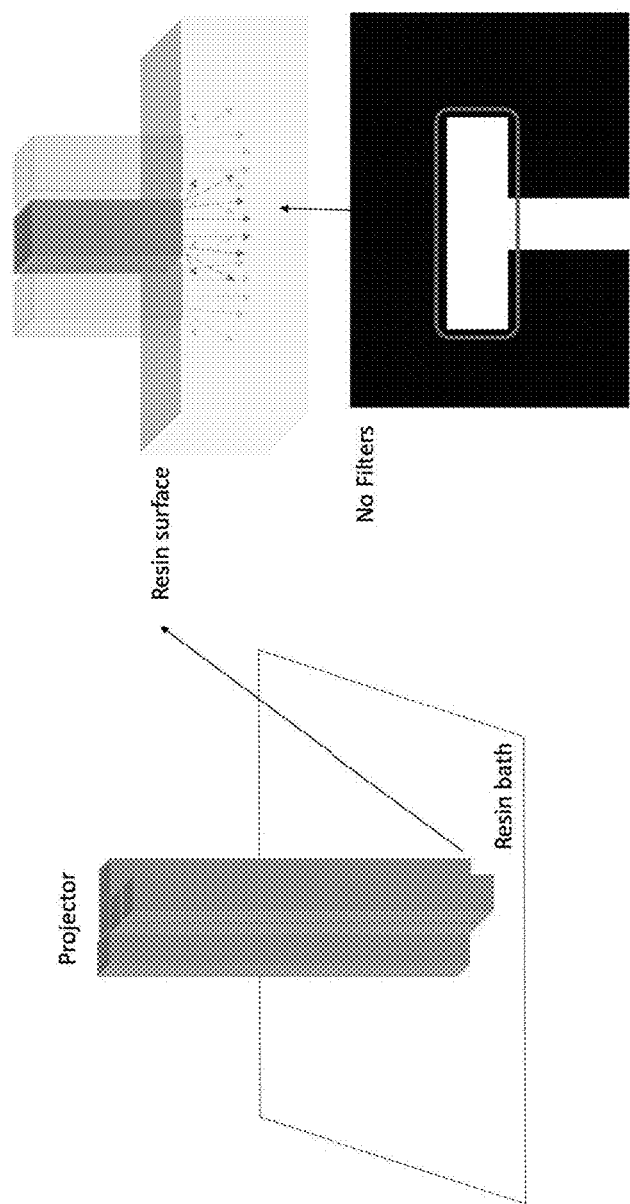
FIG. 19 shows processing of the slice where no filters have been applied.
Figure 20:
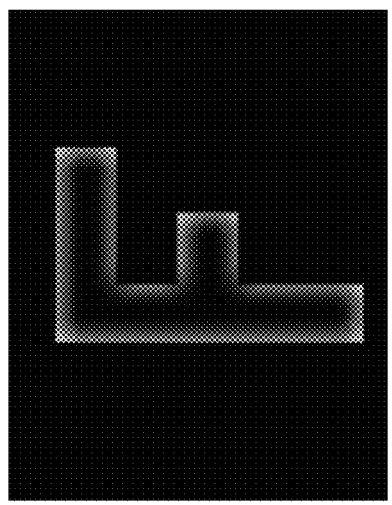
FIG. 20 shows a slice where filtering is applied, lowering the intensity of activated neighboring pixels according to various embodiments.

A typical application of optimized intensity filtering during the slicing at the compile process is the hollow gradient filter to optimize the print quality regarding light refraction within the resin for a computationally optimized homogeneous curing process. For example, FIG. 19 shows processing of the slice where no filters have been applied. As seen in the FIG. 19, without this filter, light refraction in the resin leads to initially intended light refraction and scattering of UV light and therefore scattering of curing resin in the model. Areas surrounded by other cured areas receive more UV light by light refraction, in comparison to a standalone pixel being cured. When now comparing with the effect of the hollow gradient radial filter illustrated in FIG. 20, the effect can be summarized as follows: The more activated neighbouring pixels there are and the more intense the neighbouring pixels are activated, the pixel is dimmed down. The overall result is, that pixels surrounded by high intensity projections receive UV curing light by refraction already anyways and do not need to be cured as much as stand-alone pixels being cured. For an optimized situation in this example the amount of introduced light, composed of directly projected light and refraction scatterings, is homogeneous.

Designs/Structures enabled by the process

Simple Fiber

The Wireframe structures allow creation of a large variety of fiber types efficiently.

```
Tapered hair
"Nodes": [
        "0.000 0.000 0.000",
        "0.000 5.240 9.612",
        "0.000 10.350 13.740",
        "0.000 13.744 15.743",
        "0.000 15.862 16.795",
        "0.000 17.156 17.376"
    ],
    "Wireframe":[
        {
            "p":"Square",
            "n":"1 2 3 4 5 6",
            "d":"1.0 1.0 0.5 0.25 0.12 0.06 ",
            "s":"0.0 0.0 1.0",
            "sf":"0.0 0.87 -0.47",
            "e":"0.0 0.91 0.4",
            "t":"0.0 0.0 0.0 0.0 0.0 0.0 "
        }
    ]
```

Figure 21A:
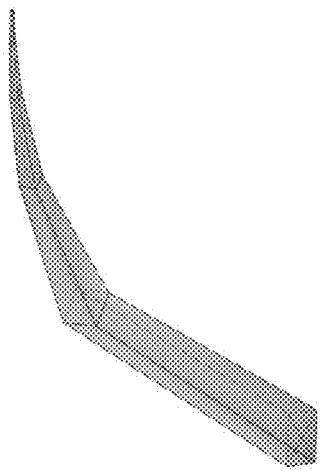
FIG. 21A shows an example simple fiber that may be created using various embodiments.
Figure 21B:
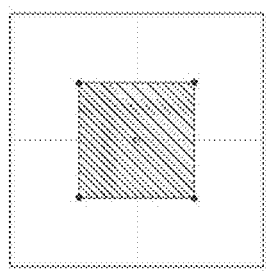
FIG. 21B shows an example cross-section of the simple fiber of FIG. 21A.

A simple example of the Wire structure would be a tapered hair. FIG. 21A shows an example simple fiber that may be created using various embodiments. FIG. 21B shows an example cross-section of the simple fiber of FIG. 21A.

With reference to FIGS. 21A and 21B, this tapered hair is defined by nodes and a series of parameters.

Nodes determine the shape of the spine. Thus this hair passes through point n1, n2, n3, . . . , n6, which reference to the coordinates listed under "Nodes". The spine can be modified by referencing to different nodes or by changing the coordinate of each node.

Figure 22:
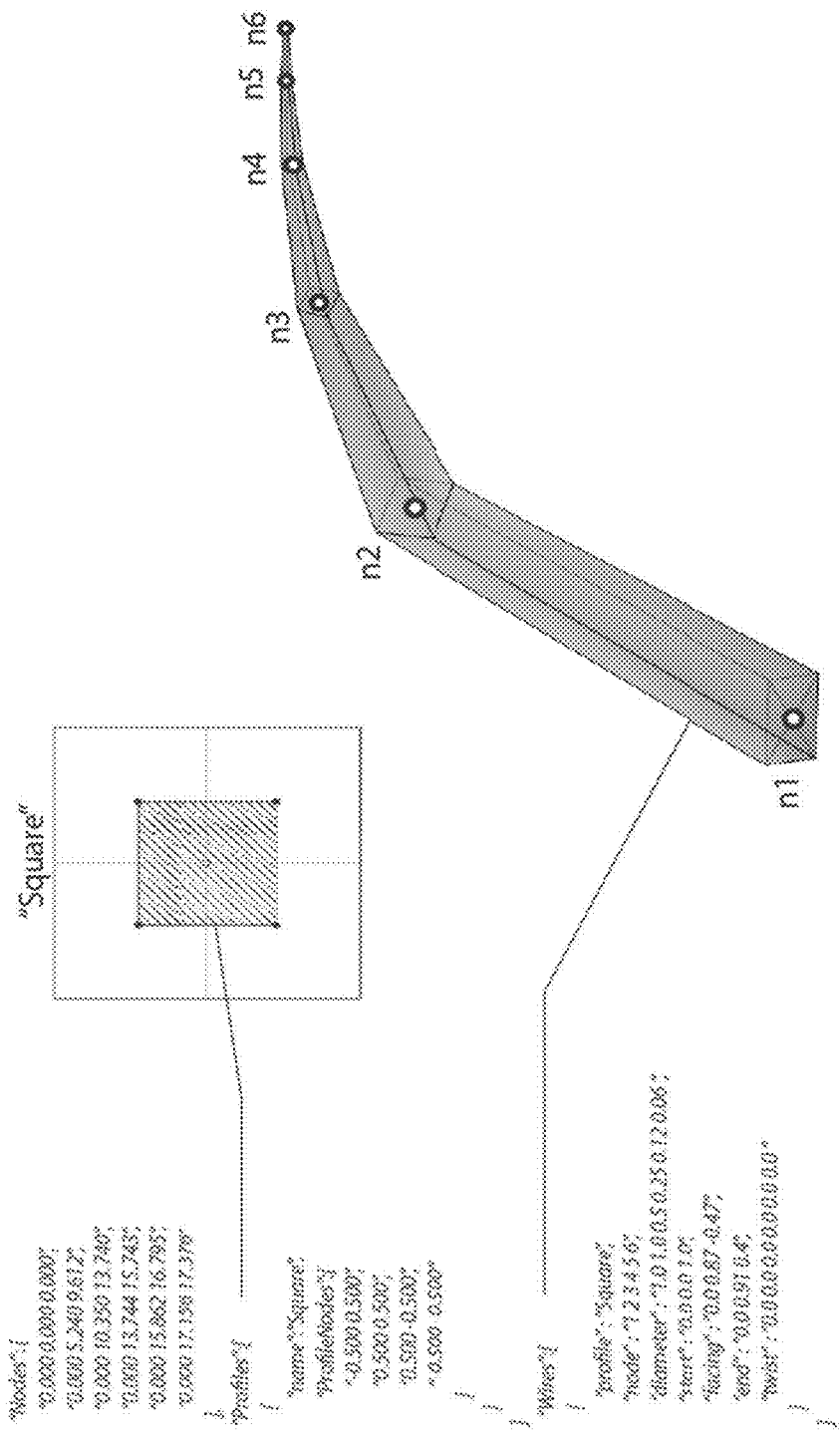
FIG. 22 shows an example data representation of a simple fiber according to various embodiments.

Parameters determine the detail shape of the hair. Profile determines the cross-sectional shapes of the hair. In this case a "Square" is chosen as shown in FIG. 22. Diameter of the hair goes from 1.0 mm at node n1, gradually to 0.06 mm at n6. The "start" normal is set to the Z-axis so the base of the hair is flush to the base plane. This hair does not twist and all values in "twist" are set to zero.

Figure 23A:
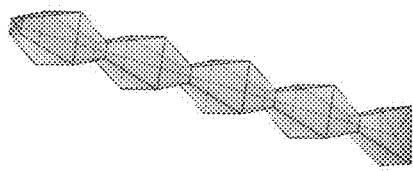
FIG. 23A shows an example nodal hair that may be created using various embodiments.
Figure 23B:
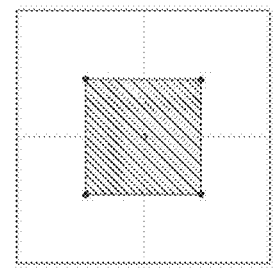
FIG. 23B shows an example cross-section of the nodal hair of FIG. 23A.

Other types of structures may be created, including, but not limited to:

Nodal hair (as shown in FIGS. 23A and 23B) and may be defined as:

```
"Nodes": [
    "0.000 0.000 0.000",
    "0.000 0.429 1.446",
    "0.000 0.858 2.892",
    "0.000 1.287 4.339",
    "0.000 1.717 5.785",
    "0.000 2.146 7.231",
    "0.000 2.575 8.677",
    "0.000 3.004 10.123",
    "0.000 3.433 11.569"
    "0.000 3.862 13.016"
],
"Lines":[
    {
        "p":"Square",
        "n":"1 2 3 4 5 6 7 8 9 10",
        "d":"1.0 0.3 1.0 0.3 1.0 0.3 1.0 0.3 1.0 0.3 ",
        "s":"0.0 0.0 1.0",
        "sf":"0.0 0.95 –0.28",
        "e":"0.0 0.28 0.95",
        "t":"0.0 0.0 0.0 0.0 0.0 0.0 0.0 0.0 0.0 0.0 "
    }
]
```

Figure 24A:
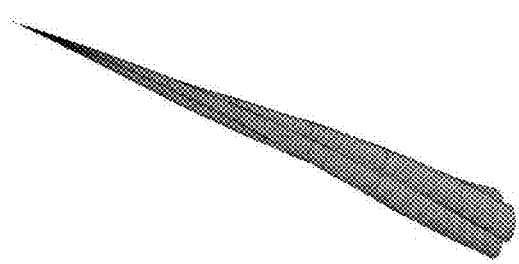
FIG. 24A shows an example twisted hair that may be created using various embodiments.
Figure 24B:
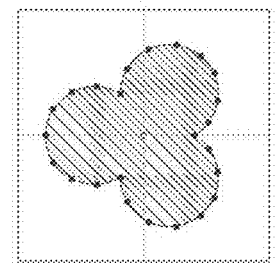
FIG. 24B shows an example cross-section of the twisted hair of FIG. 24A.

Twisted hair (as shown in FIGS. 24A and 24B) and may be defined as:

```
"Nodes": [
    "0.000 0.000 0.000",
    "–0.246 0.552 1.859",
    "–0.492 1.104 3.719",
    "–0.738 1.655 5.578",
    "–0.984 2.207 7.437",
    "–1.230 2.759 9.297",
    "–1.476 3.311 11.156",
    "–1.722 3.862 13.016"
],
"Lines":[
    {
        "p":"Trefoil",
        "n":"1 2 3 4 5 6 7 8",
        "d":"1.0 0.85 0.71 0.57 0.43 0.29 0.15 0.01 ",
        "s":"0.0 0.0 1.0",
        "sf":"0.03 0.95 –0.28",
        "e":"–0.12 0.28 0.95",
        "t":"0.53 0.53 0.53 0.53 0.53 0.53 0.53 0.53 "
    }
]
```

Fur

Figure 25:
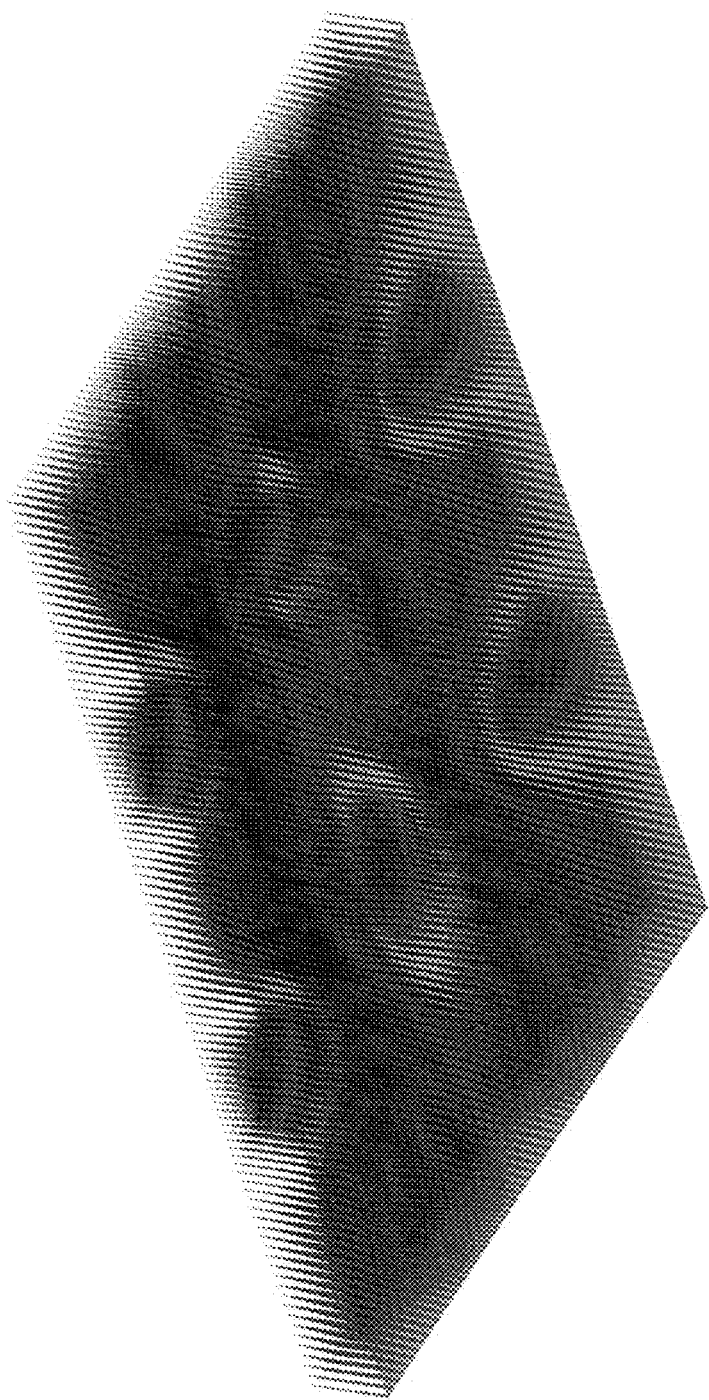
FIG. 25 shows an example of applying multiple populate functions to a same mesh face according to various embodiments.
Figure 26:
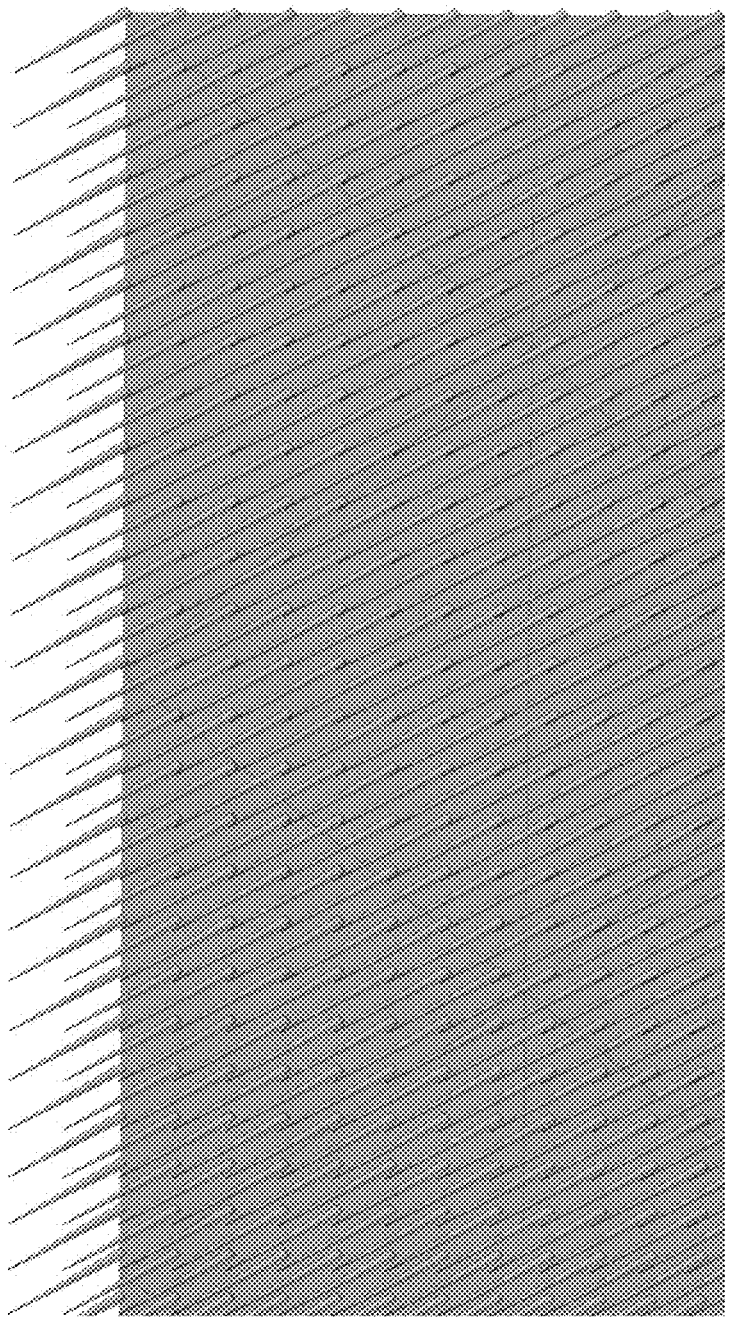
FIG. 26 shows a uniform populate function showing hairs applied to a surface.

Dense fur can be achieved in multiple ways with the .MESO file format, with different effects on fidelity and data efficiency. For example, every hair can be represented as a separate wireframe. In this case, each hair will have its unique parameter that would allow a feature control down to individual hair. Alternatively, the format can represent a collection of hair as Populate function of Shell faces. With this method, only a small number of geometry information is required to describe a larger collection of hair. Multiple Populate functions can be assigned to the same mesh face to overlapped effects. FIG. 25 shows an example of applying multiple populate functions to a same mesh face according to various embodiments. FIG. 26 shows a uniform populate function showing hairs applied to a surface.

Feather

Like the fur example above, highly detailed and dense structure could be created by representing all geometries as a wireframe, or using parametric function supported by the .MESO format to achieve compact data. In the case of feather, the Branching function can efficiently encode the fractal structure. Simple Wireframe can be branched out to create a feather. If the child wireframe also contains Branching function, this fractal branching can repeat over several layers.

Figure 27:
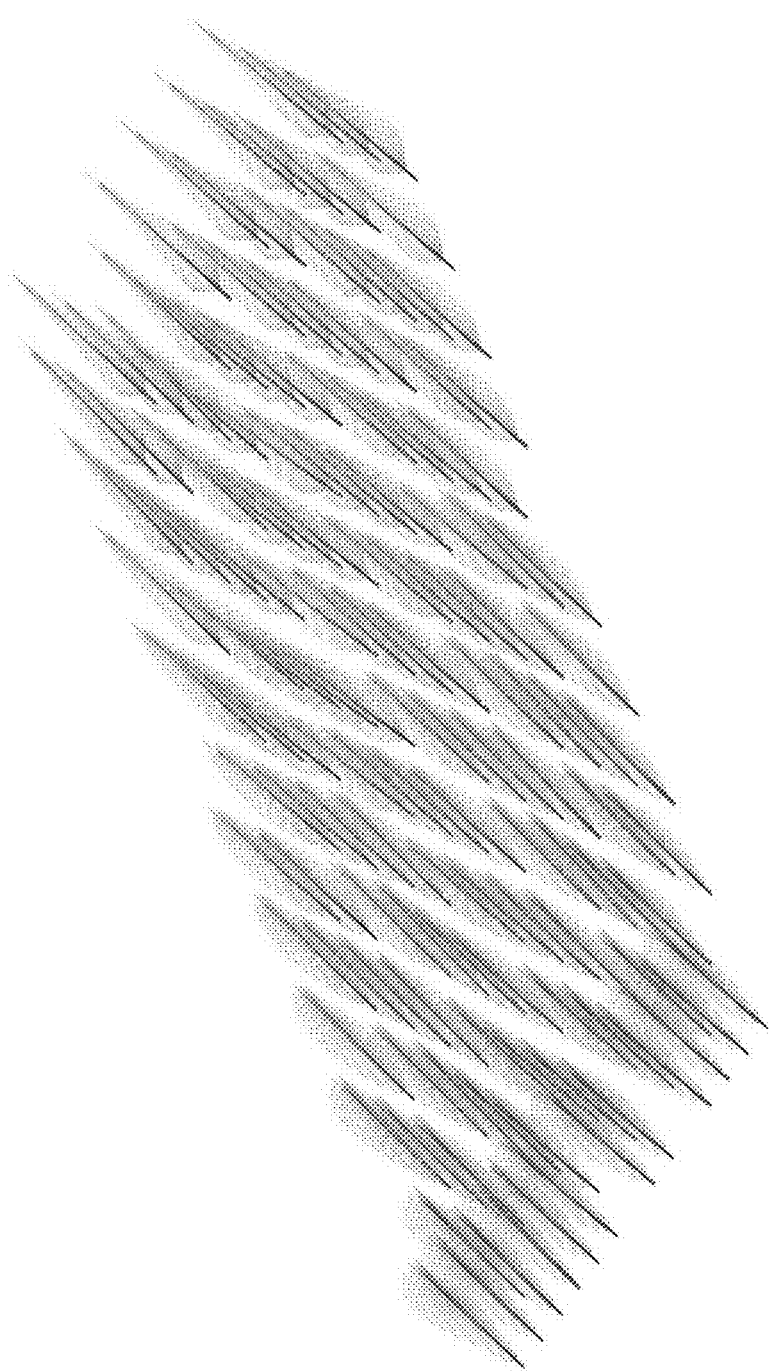
FIG. 27 shows an example feather layout containing a number of blended geometries each containing different weights.
Figure 28A:
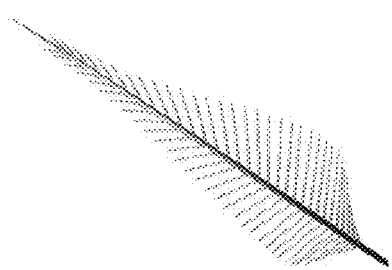
FIGS. 28A-28B show two different parent geometries used to generate the feather design layout shown in FIG. 27.
Figure 28B:
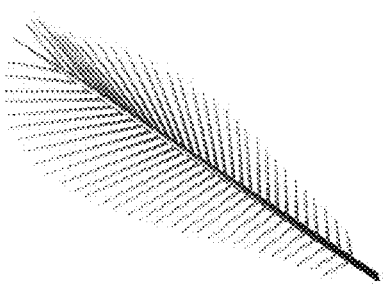

The example in FIG. 27 shows a feather layout design containing 129 Blended geometries, each contains different weights for Parent geometries. The two parents shown in FIGS. 28A-28B are Wires containing their own Branching function.

Lattice

Figure 29:
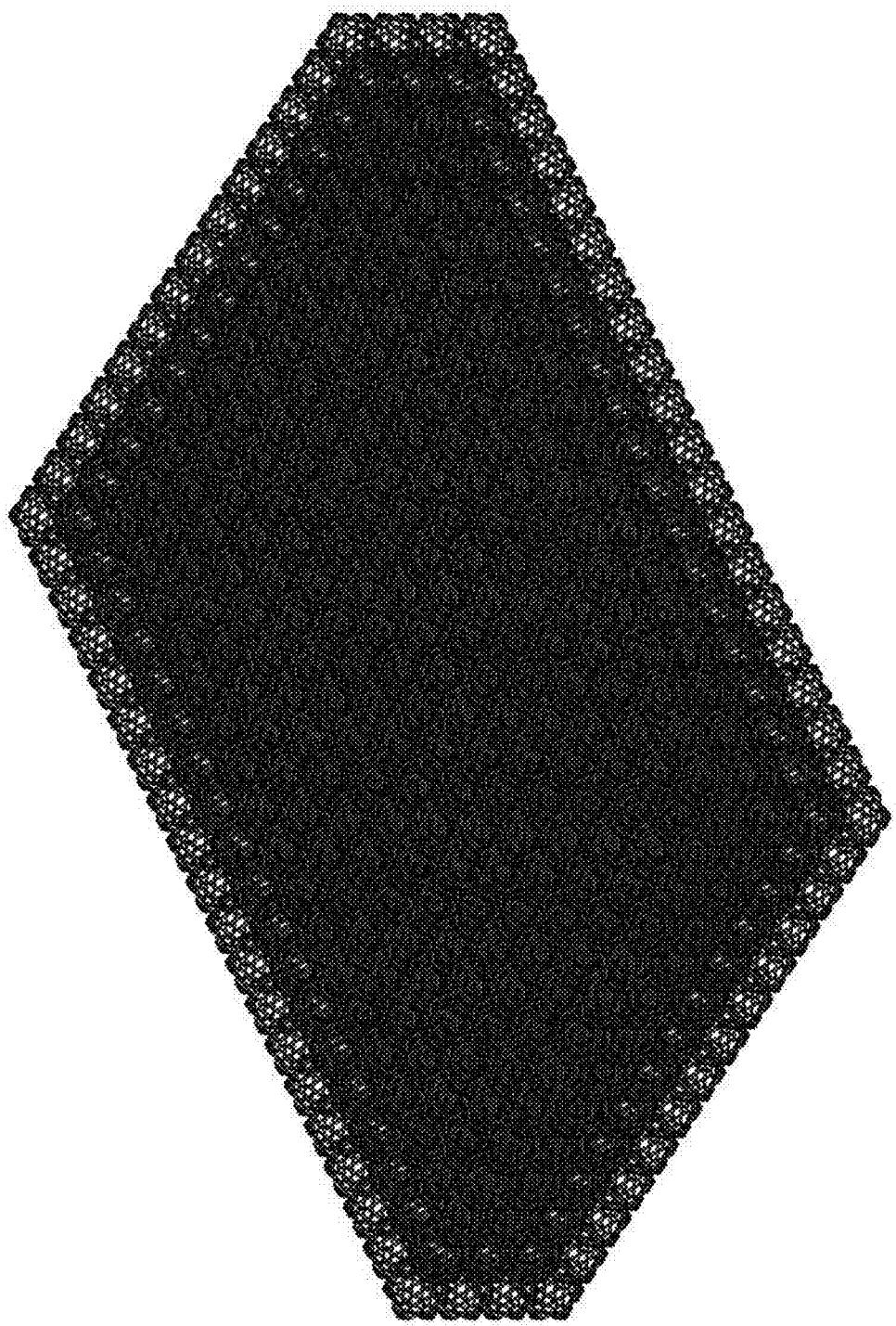
FIG. 29 shows a lattice structure that can be generated using a modular unit such as that shown in FIG. 30.
Figure 30:
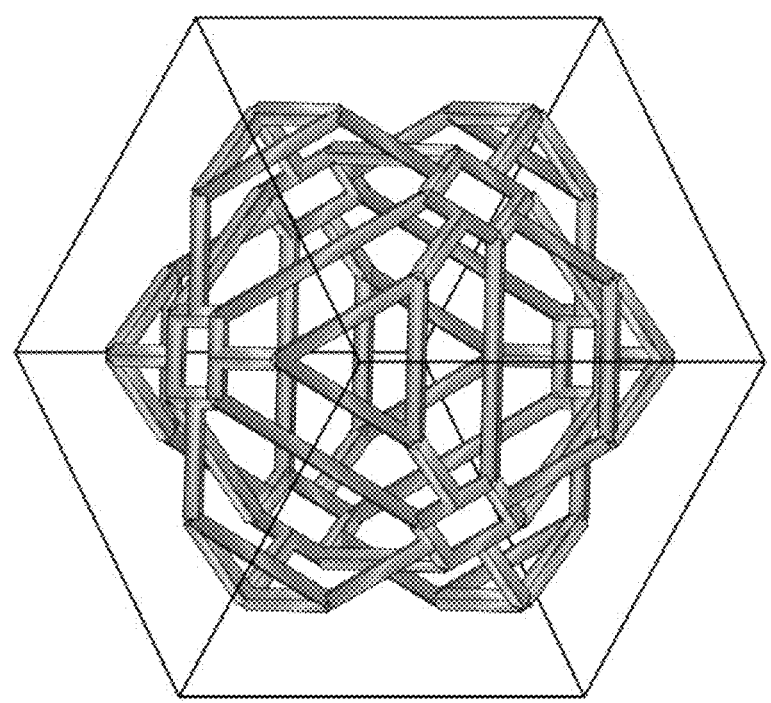

Lattice geometries could be generated by populating Box Mapping with modular units. The modular unit is captive in one-unit size box, which is then remapped onto a series of box mapped by 8 nodes in the Volumetric Mapping functions. FIG. 29 shows a lattice structure that can be generated using a modular unit such as that shown in FIG. 30.

Woven

Figure 31:
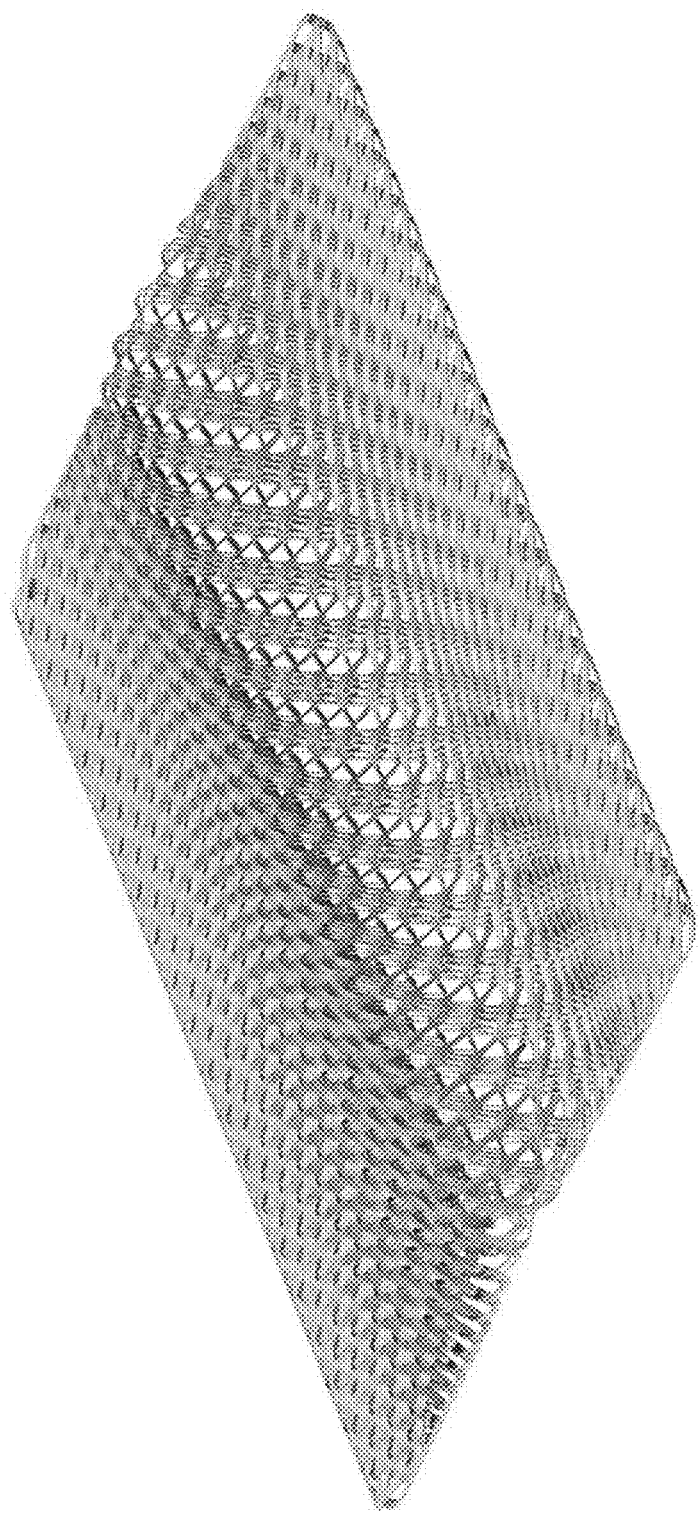
FIG. 31 shows a woven structure that can be generated using a mapping weave unit as shown in FIG. 32.
Figure 32:
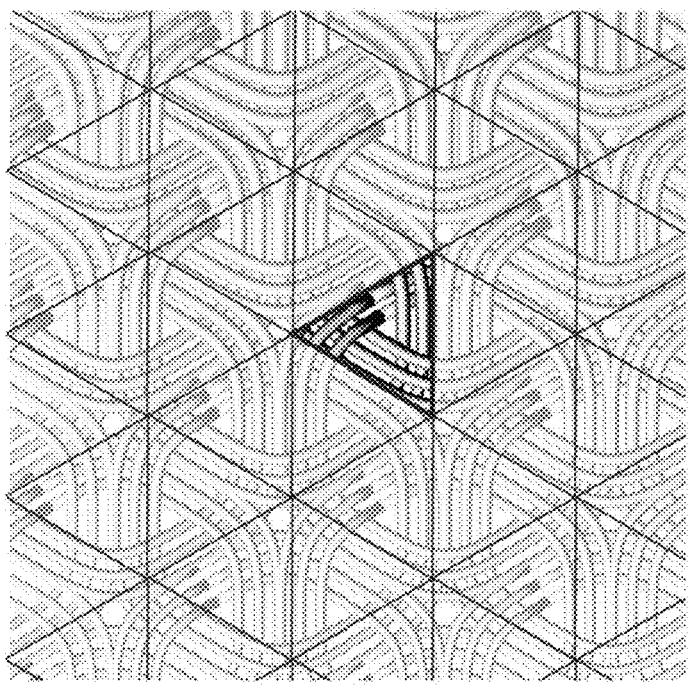

A woven structure as shown in FIG. 31 can be achieved by mapping weave unit modules (e.g., as shown in FIG. 32) onto a Shell with varying thickness and Shell Face size. In this case, the entire weaving structure could be efficiently represented by 6 wires and one Shell.

Swab

Figure 33B:
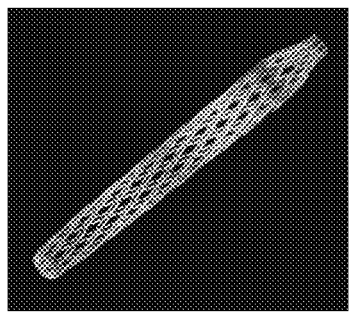
FIGS. 33A-33D show a number of 3D lattice structures that can be combined to generate a swab structure such as that shown by way of example in FIG. 34A-34B.
Figure 33D:
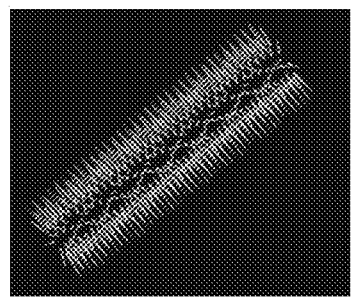
Figure 33A:
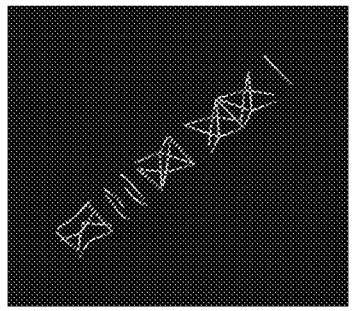
Figure 33C:
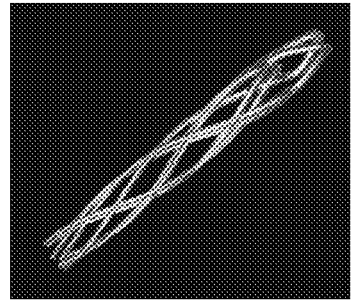
Figure 34A:
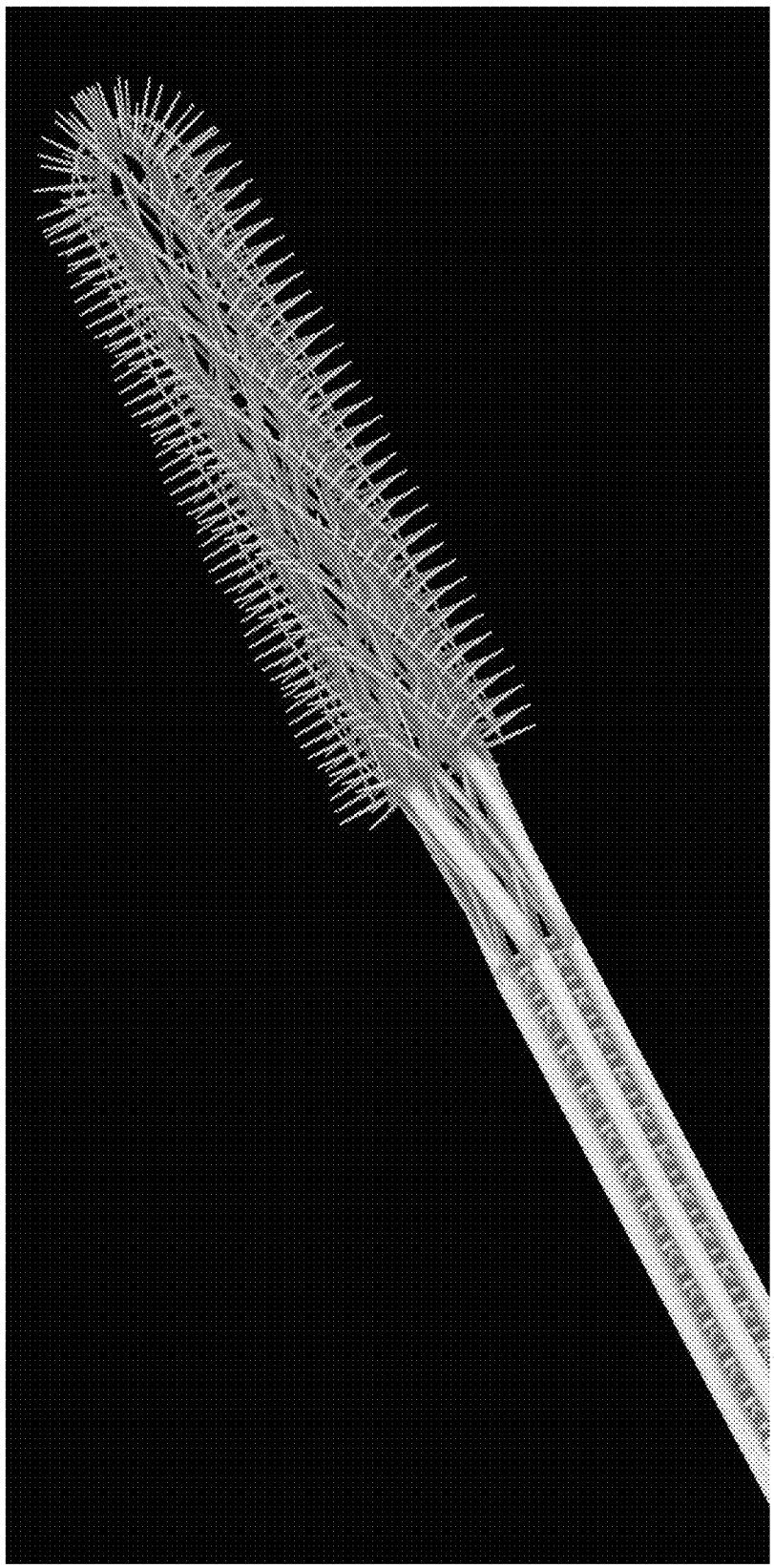
FIG. 34A-34B shows the entirety of an example swab structure.
Figure 34B:
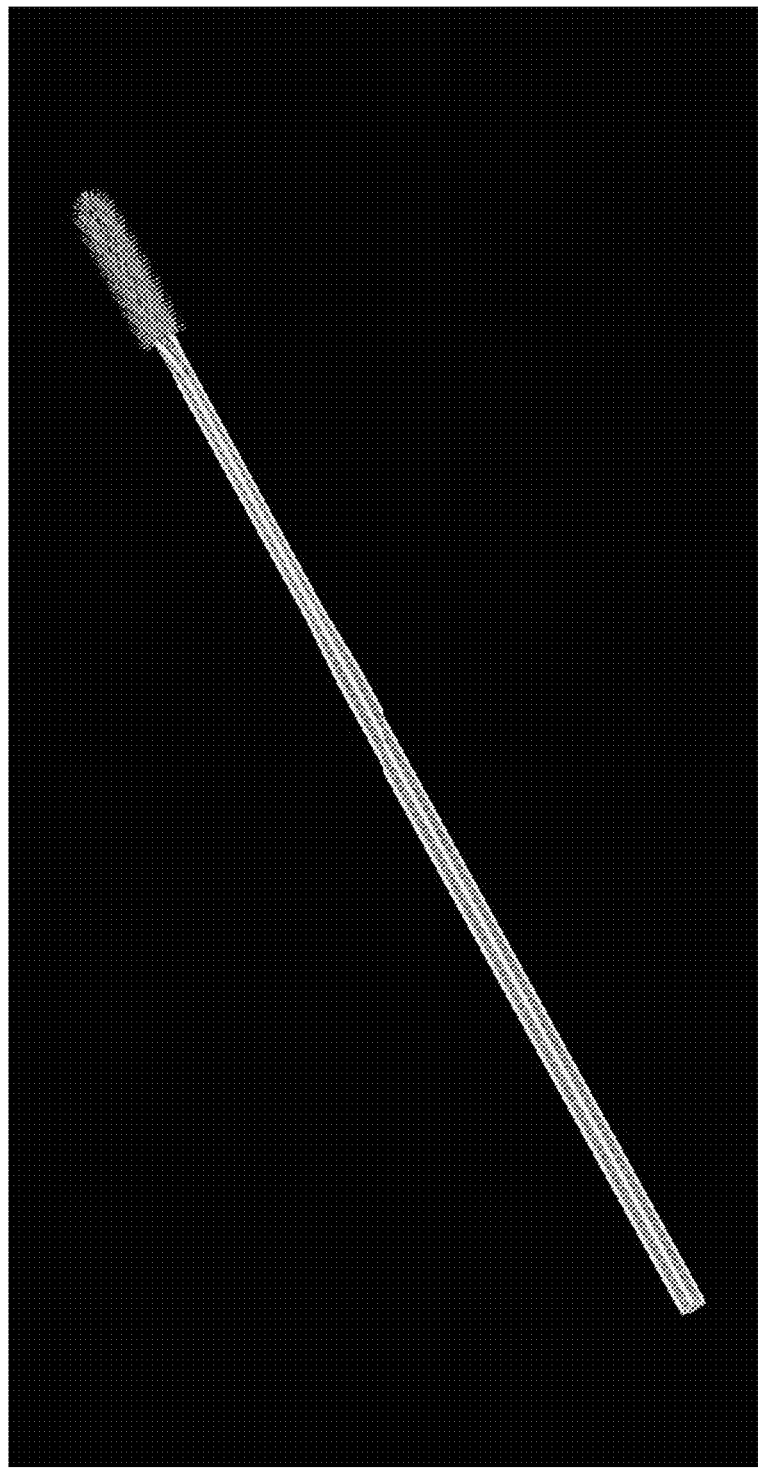

A swab design like the one shown in FIGS. 34A and 34B can be achieved by a collection of Wires. The construction of the bulb may include 1) interior 3D lattice structures that provide structural rigidity and assist fluid retention as shown in FIG. 33A, 2) net structure that define the overall shape and enable absorption as shown in FIG. 33B, 3) reinforced element of the net structure to secure integrity of the bulb as shown in FIGS. 33C and 4) a spiral array of fine hairs that sit on the net structure as shown in FIG. 33D. Each hair array is reinforced at their midsection with a thin spine.

Figure 35:
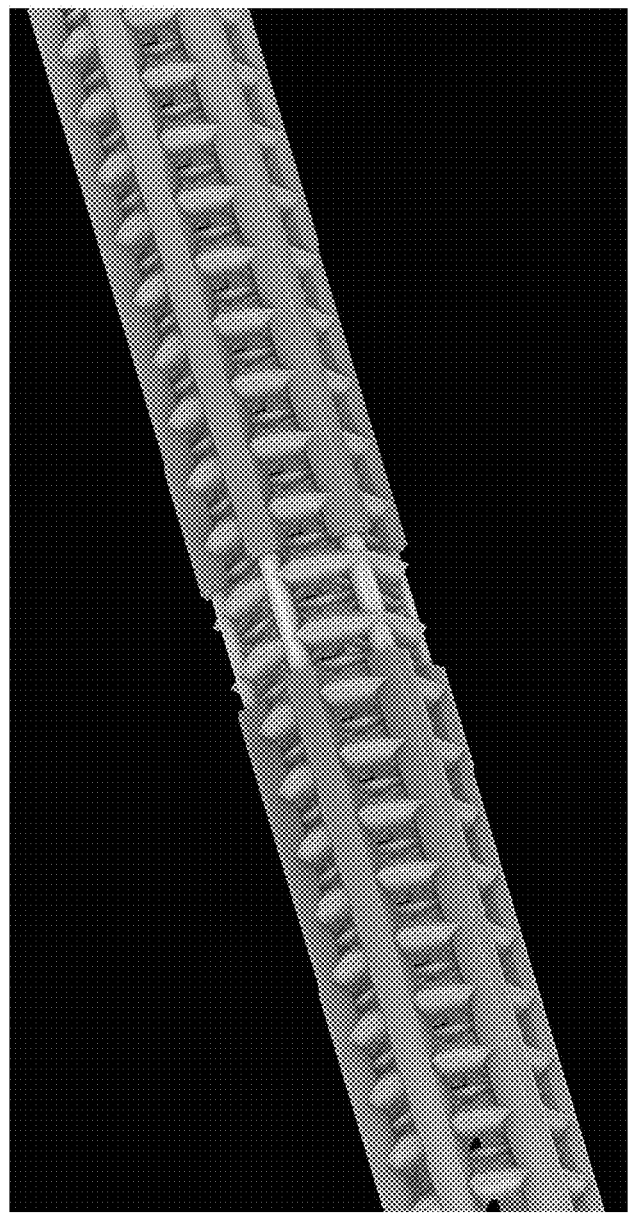
FIG. 35 shows an example shaft structure according to some embodiments.

Construction of the shaft of the swab shown in FIGS. 34A-34B may be constructed using 1) Parallel strands of Wires that are bounded together and reinforced by 2) loops and diagonal bracing between each strand. In the example shown in FIG. 35, the Shaft features a break off point, achieved by reducing diameter of a short section of the parallel strand at the break off point. An alternative shaft construction is made up of 1) gridded shaft wall structures as primary structure, 2) interior shearing reinforcement element, 3) spiralling texture curve as finishing on the outside surface.

Figure 36A:
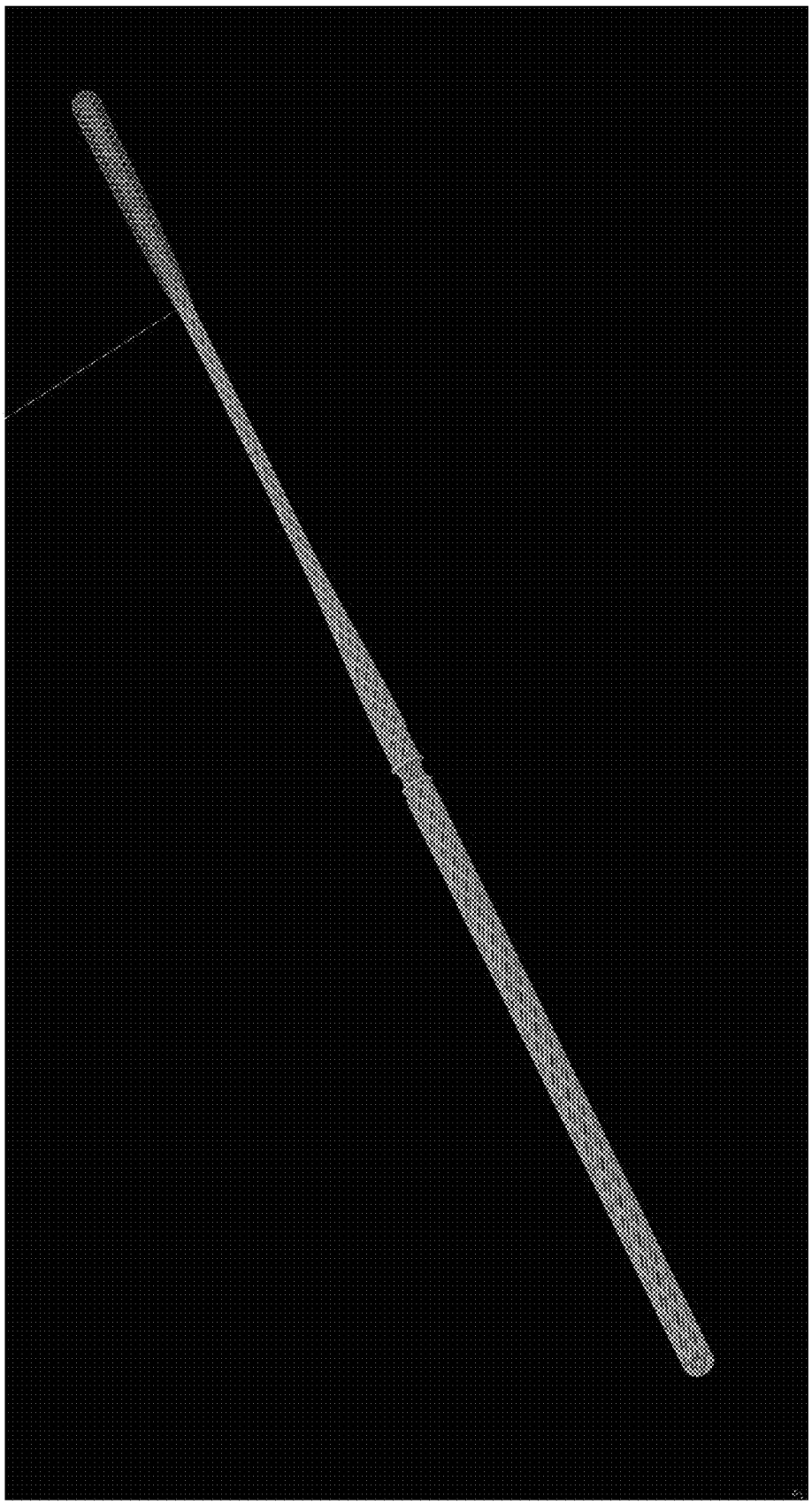
FIGS. 36A-36B show other embodiments of a swab design.
Figure 36B:
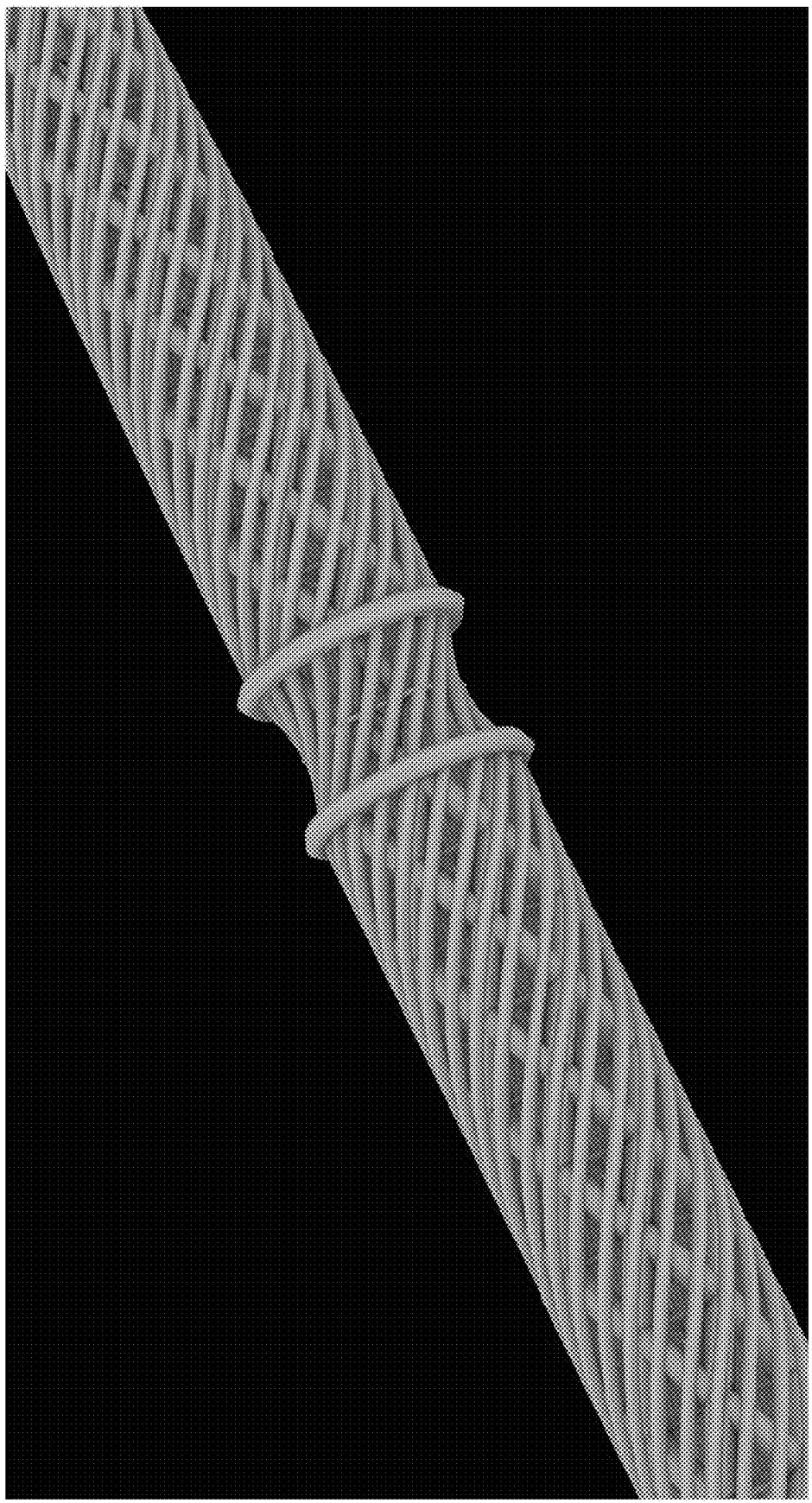

In an alternate construction of the shaft as shown in FIG. 36A, the shaft includes 1) a primary structure made up of line element in a diamond grid pattern in a cylindrical form, 2) a secondary structure made up of an internal spiraling surface attached to a diamond grid, that provides internal shearing resistance, and 3) a texture finish made up of a thinner line element spiraling on the exterior to provide refined finishing. FIG. 36B shows a break off point, which includes a reduced diameter at a break-off point.

Regarding construction of a bulb, Line elements of lattice and hair may be curled in an S-shape to provide bounciness and compliance. Stiffness of the bulb may be determined by controlling the combination of these factors; spacing of hair, diameter of hair, curvature/S-shape of hair, density of primary and secondary net structure, and diameter of net structure lines. In general, denser the structure with elements close to each other, stiffer the bulb would be; thicker the line elements, stiffer the bulb would be.

Diameters of an example hair structure or net structure could vary, for example, between 300 µm to 50 µm. Opening of an example net structure could be varied to control fluid absorption and release. Opening size of the net could vary from 2 mm to 100 um.

By varying the property of the structure of the shaft, different stiffness could be achieved. For example, the neck region of the shaft has a smaller overall diameter. Diamond grid is elongated along the length of the shaft. Line elements are thinner and internal spiraling surfaces are narrower. This results in a flexible and soft region of the shaft that could bend around a tight radius. Vice versa, a stiff and rigid handle region could be achieved with opposite properties.

Break points can be introduced at any location along the shaft. The break point is a narrow region of increased brittleness. This is achieved by reduced line element diameter and reducing overall diameter. This creates an hourglass shape region that also increases torsion force. This region is visually emphasized with rings on both ends of the region for easy identification.

Indicators can be introduced at any location along the shaft. The indicator is an enlarged region of the shaft. Additional line elements are added on top of the existing shaft instead of altering shaft structure. This help maintain uniform stiffness of the shaft. Additional line elements arranged in a diamond grid pattern form the indicator structure.

Regarding design workflow, shape of the bulb could be freely defined by a bounding volume. Together with length and location of break point and/or indicator, if any, and desired diameter of functional parts, these information are fed into a parametric modelling software that construct the MESO structure and assign corresponding value to each line element.

Figure 36C:
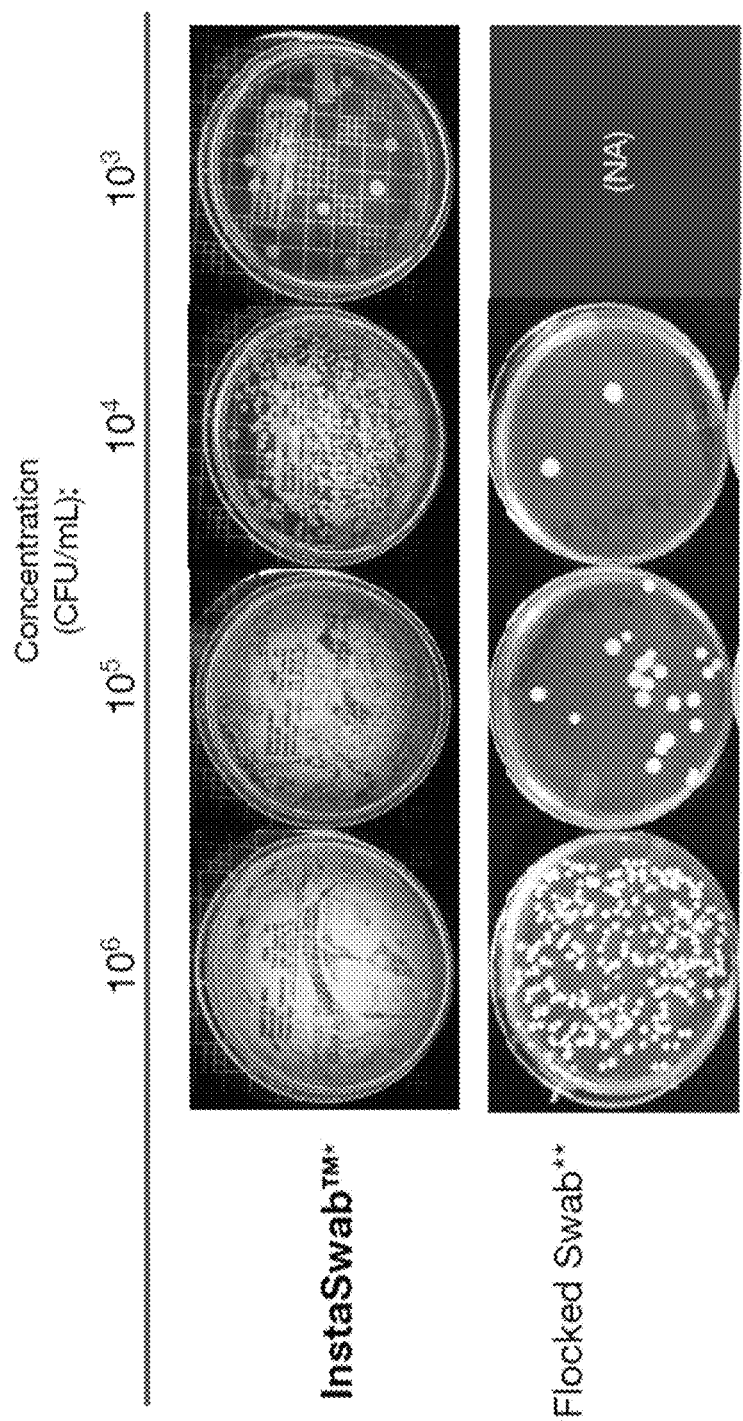
FIG. 36C shows experimental results of a swab design as described herein and shown in FIGS. 36A-36B versus a conventional flocked swab.

As shown in FIGS. 36C-36D, swabs (termed InstaSwabs) created using at least some of the methods described herein, may outperform other types of swabs such as those used for medical applications, such as flocked swab as well as cotton swabs used for mid-turbinate, anterior or nasopharyngeal swabs, to fit a variety of applications including at-home testing kits. Lab results show that such swabs have a higher liquid/solid separation rate than conventional cotton swabs, and a higher microbial transfer efficiency than market leading flocked swabs. FIG. 36C shows a bacteria elution test that evaluates how efficiently a swab can collect and release bacteria samples. Bacteria samples are collected with a swab. The sample is released into a medium which is then diluted into a series of concentrations. From each concentration, a number of bacteria units are counted that grow into living colonies (colony forming unit, or CFU). As shown in the FIG. 36C, each bright spot on the agar plate is a bacteria colony. A good swab releases so many living bacteria that after extensive dilution, it is still possible to detection them. This is one of the most important criteria for disease diagnostics: finding enough pathogens to test.

Cosmetic Applicators

Cosmetic applicators such as mascara brushes, foam applicator, brushes, etc., can be achieved by a collection of Wires. The .MESO format enables a high degree of customization of bristle characteristics unique to cosmetic applications, which include 1) bristle hair diameter, 2) bristle hair spacing, 3) product retention, 4) overall geometries.

Figure 37:
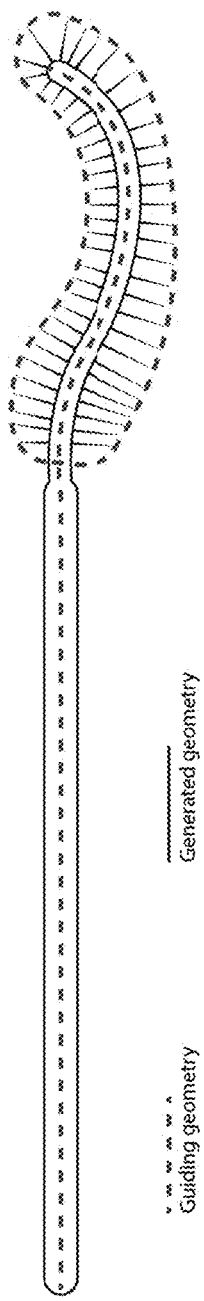
FIG. 37 shows an example cosmetic applicator design according to various embodiments.

This cosmetic applicator shown in FIG. 37 includes 1) a dense lattice core as primary structure, 2) bristles of various length and diameter developing from lattice core, 3) reinforcement wires that run between mid sections of bristle, 4) a shaft handle made up of dense lattice structures.

Customization of the design may be facilitated by MESO file format, with a simplified representation of wires with a base curve. Features of the applicator are procedurally generated by guiding geometries by the following steps. 1) The lattice core of the bulb and shaft is created by offsetting a shell around a 3D free-form curve. 2) Wire structures grow out of the central core around a specified range of angles around the axis of the core. 3) A free-form 3D bounding geometry defines the trimming length of each wire structure. 4) Diameter and profile of each wire is individually defined in its MESO data. This enables a high degree of customization of overall geometry.

Figure 38:
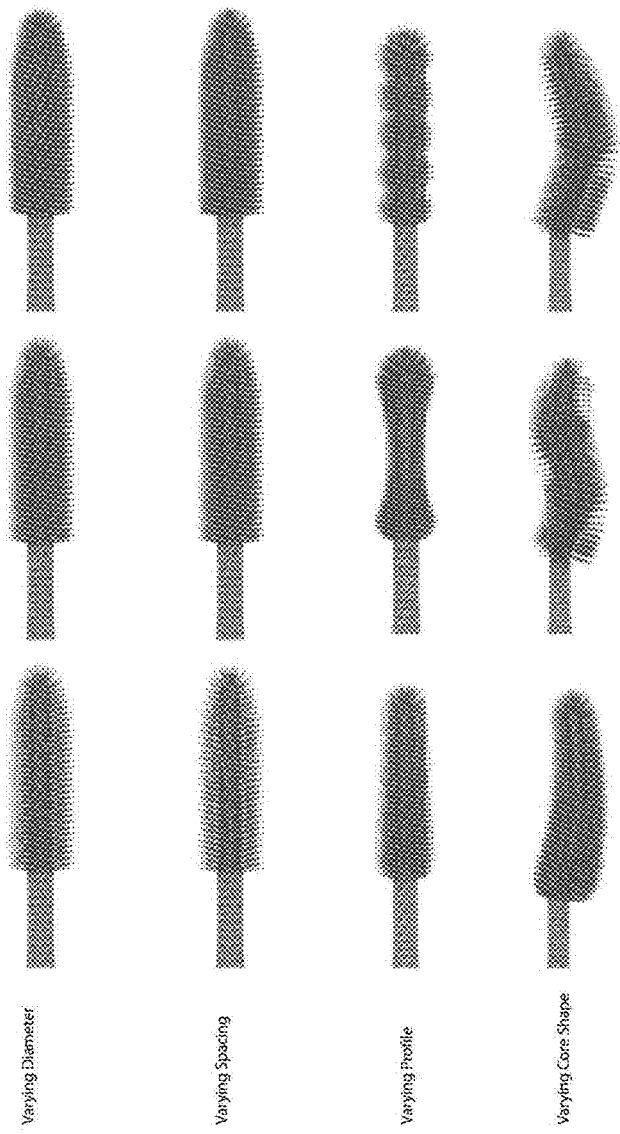
FIG. 38 shows varying cosmetic applicator designs according to various embodiments.
Figure 39A:
FIGS. 39A-39C show various other types of cosmetic applicators according to some embodiments.
Figure 39B:
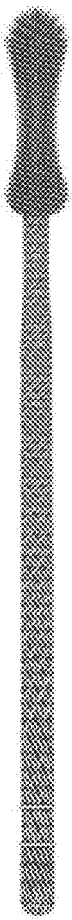
Figure 39C:

Customization varies from application to application. For instance, in the case of mascara brushes, various parameters may be adjusted to suit the application of mascara. For instance, Bristle spacing can be adjusted to control deposition of mascara fluid. For example, sparser spacing enables a heavy application and vice versa. Position and thickness of reinforcement wires control fluid retention on the brush. FIG. 38 shows varying cosmetic applicator designs according to various embodiments, having different diameters, spacing profiles and core shapes. FIGS. 39A-39C show various other types of cosmetic applicators having different brush shapes according to some embodiments.

False Eyelashes

Making of a false eyelash is a highly labor-intensive operation. However, the inventors appreciate that the same or a superior product can be achieved by a collection of wire and can be 3D printed. The wire structure may be used to represent an array of wire with customizable curvature and thickness. In combination with the RAMP system, a lash thickness from 0.05 to 0.15 mm can be achieved, which approximates existing synthetic monofilament lashes.

Figure 40:
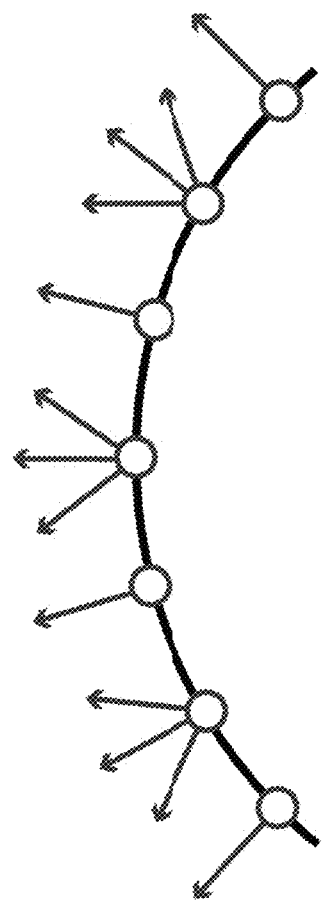
FIG. 40 shows an example design of an eyelash using a wireframe representation.
Figure 40:
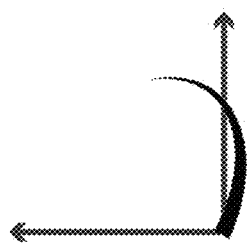
Figure 41:
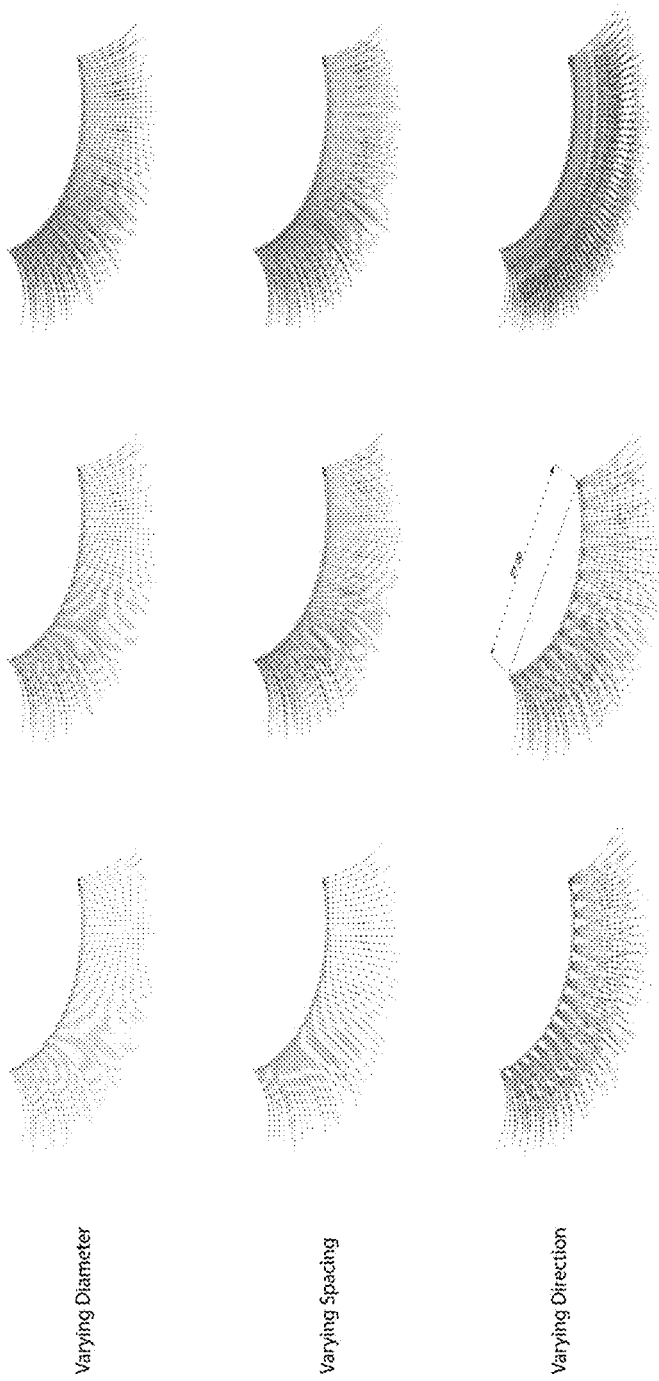
FIG. 41 shows varying eyelash designs according to some embodiments.

In some embodiments, customization may be facilitated by MESO file format, with a simplified representation of wires with a base curve. Features of the eyelash may be procedurally generated by the following steps. 1) A 3D free-from wire forms the base strips. 2) A series of normalized values and vectors define the base position and direction of each eyelash. 3) 3D free-form wires are transposed onto each position and align to corresponding direction. FIG. 40 shows an example design of an eyelash using a wireframe representation. FIG. 41 shows varying eyelash designs according to some embodiments.

Support

Support structures are sacrificial structures that provide stability and anchor points for print objects. It also provides These structures are typically removed and discarded. Support structures use the same data structures as other geometries, but are labeled with a unique flag.

In some embodiments, there are three types of support structures, 1) pillar support, 2) frame support and 3) Leading edge support.

Pillar Support

Pillar supports are tapered Wires that are typically anchored on substrate/convenient locations of other print parts and contact the print part with a minimum footprint.

Pillar supports are mostly perpendicular to the resin level. This minimizes deflection, given the slight buoyancy of cured resin. In some embodiments, the diameter of the contact point goes between 0.05 to 0.1 mm for various degrees of attachment strength. The small contact point rapidly grows into a thicker shaft. The shaft is either anchored to the substrate with a larger footprint, or lands on top of another print with a minimum footprint.

Figure 42:
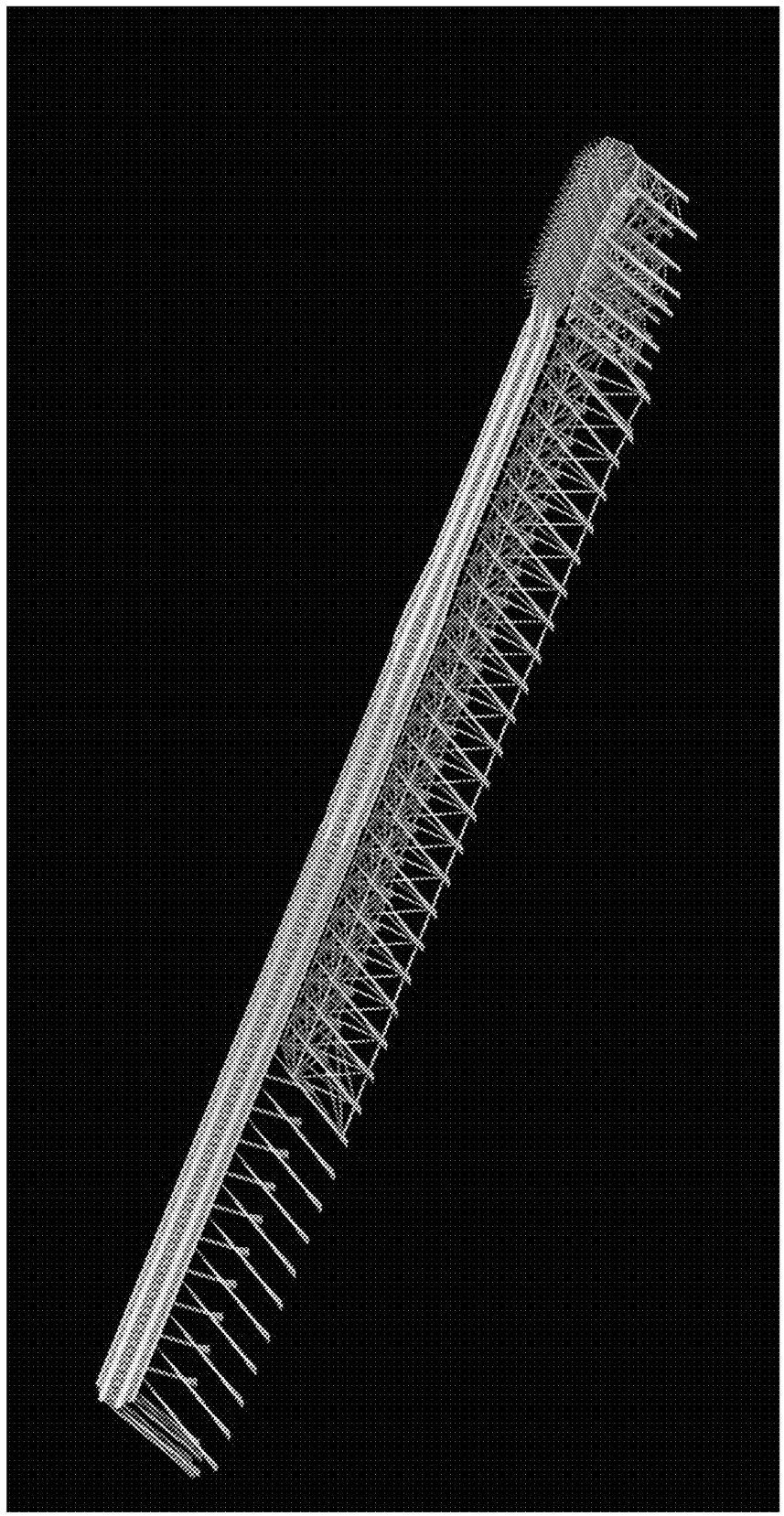
FIG. 42 shows pillar support techniques using wireframe representations according to various embodiments.

Along the length of a long print, a gradient pillar support array can be used to account for curvature of the resin vet. Thinner supports are used towards the front of the print, which would collapse and deform as it reaches curvature at the bottom of the resin vet, while thicker, diagonally braced support are used towards the end of the print, which remain rigid. The gradient in rigidity allows the support structure to collapse sequentially in a predictable manner. FIG. 42 shows pillar support techniques using wireframe representations according to various embodiments.

Frame Support

Frame supports are net-like structures formed by Wires, which provide anchor points for overhanging hair.

Overhang refers to parts of the print that are not built upon a previously printed layer. Overhangs of continuous surfaces can be handled by Pillar support, since smooth surfaces usually have small numbers of apexes that require support. However, fine, dense fur that overhang cannot be supported by Pillar support, as it would produce an equally dense array of Pillar support that would fuse into a larger solid, which is difficult to remove and uses a large amount of resin.

Figure 43:
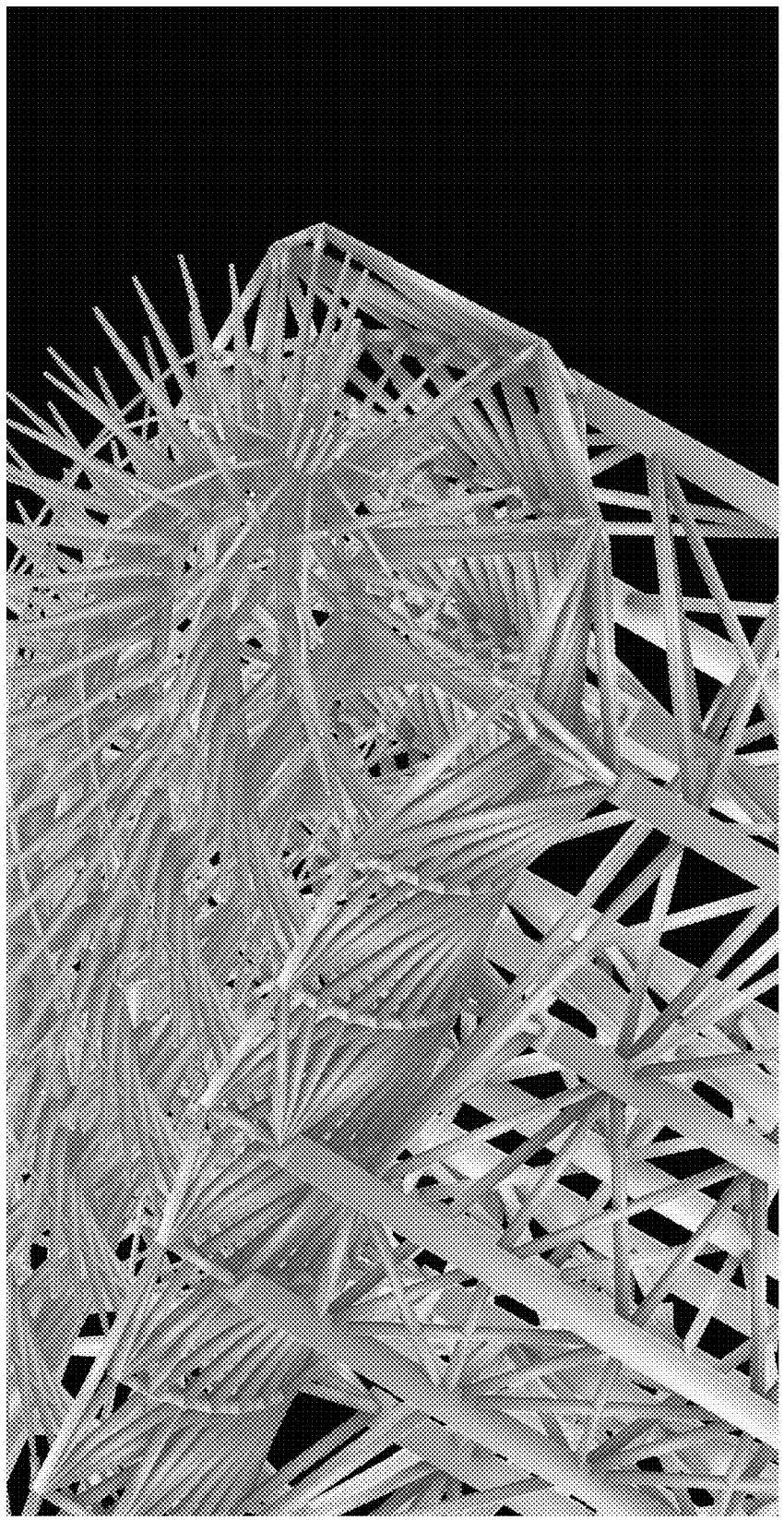
FIG. 43 shows frame support for anchoring overhanging hair according to some embodiment.

Frame support reciprocates the tip of each overhanging hair with each node of its net-like structure. This forms a cocoon around all overhang hair, and the cocoon is anchored with tree-like structures. The perforation of Frame support also minimise obstruction to resin flow. FIG. 43 shows frame support for anchoring overhanging hair according to some embodiment.

Leading Edge Support

Leading edge supports are integrated lattice-like structures with the main purpose of providing good print anchorage at the beginning of the printing process.

In most conventional DLP/SLA printing processes, printing direction is perpendicular to resin level. build platform adhesion is typically handled by building up some sort of scaffolding structures vertically from the build platform to the print. It holds the print in place against the force of gravity and pulling forces from newly cured layers. This is also important for prints with irregular shapes which could not sit flush on the build platform. These adhesion scaffolding structures also provide anchor points where overhanging surfaces grow out from.

Contrary to conventional systems, OPT RAMPS uses a roll-to-roll cDLP configuration, which resin level is at an angle to print direction (usually 45 degrees). A spacing between the substrate and the print also need to be kept for best print quality. This introduces a unique challenge to the "build platform adhesion" problem. The angle between printing direction and resin level exposes the adhesion scaffolding structure to shearing forces. The spacing also implied most prints are suspended without direct contact with the substrate.

Leading edge support is a substitute structure for print bed attachment structure in conventional vertical printing. The leading edge provides an anchoring area that is perpendicular to the printing direction yet elevated from substrate. Branching structures allow ample resin flow while increasing support footprint and support density.

Cocoon Support

Figure 44:
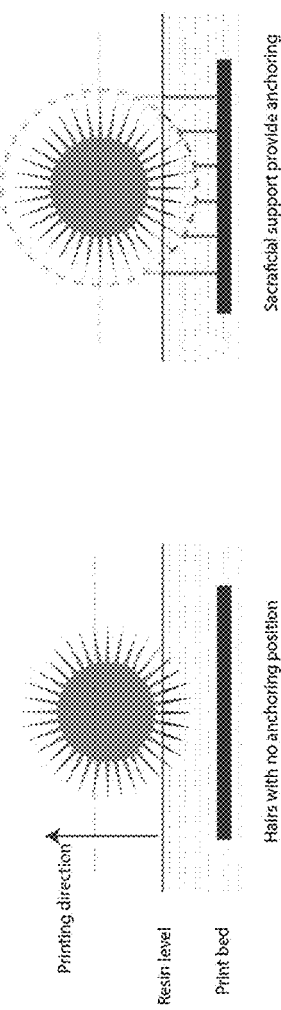
FIG. 44 shows an example cocoon support strategy according to various embodiments.

Quality of printed structure, particularly small features and fine hair, is highly dependent on printing orientation. Structures that are perpendicular to resin level yield best result while cantilevering structure and overhangs require support structures. Conventionally, these conditions are resolved by pillar support structures, which provide anchorage for surfaces to grow from. However, pillar support does not apply to fine hair structures individually supporting each hair would create dense structures which are inefficient. Many applications such, as brushes, have fine hair structure that point at multiple/opposite directions. This cocoon support strategy can support a large amount of fine hair structure with a thin, porous mesh, which in turn is supported by pillars. FIG. 44 shows an example cocoon support strategy according to various embodiments.

The generation of cocoon support is uniquely enabled by the MESO file format as direction of lines and overhang are easily detected by taking a dot product to printing direction, which signifies parallelity. The mesh can also be extracted from MESO Wire data, where the tips of hairs form nodes of the triangulated mesh.

Tiny support pillar can grow from the mesh which interfaces fine hair structures. Tapering of both the support and hair create pinch points at their intersection, forming a convenient breaking point to facilitate detachment. These small hairs also absorb irregularity between adjacent hair length, resulting in a smoother cocoon mesh.

Cocoon mesh provides extra protection to all fine structures and facilitates the correct shape formation. Cocoon acts as a flow shield that regulates flow of resin, reducing local turbulence and enabling a smooth natural recoating. It also increases local resin temperature and facilitates resin curing.

Figure 45A:
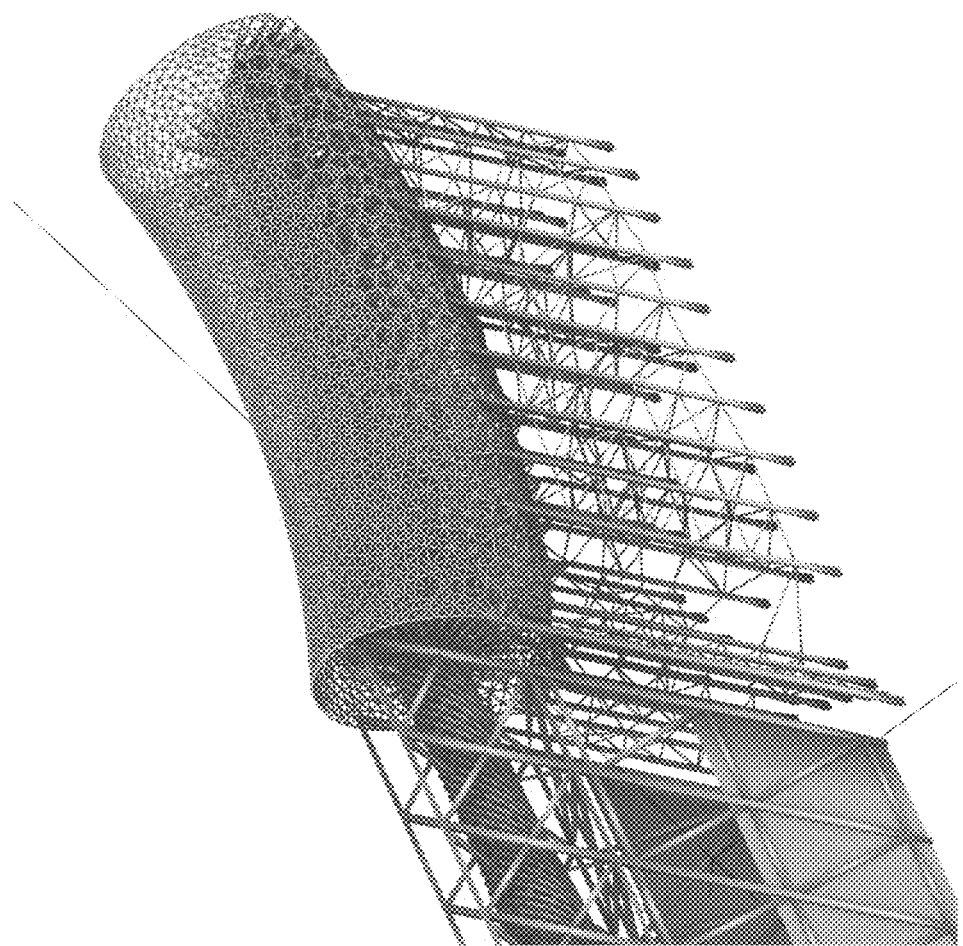
FIGS. 45A and 45B show examples of a cocoon support and cross section respectively.
Figure 45B:
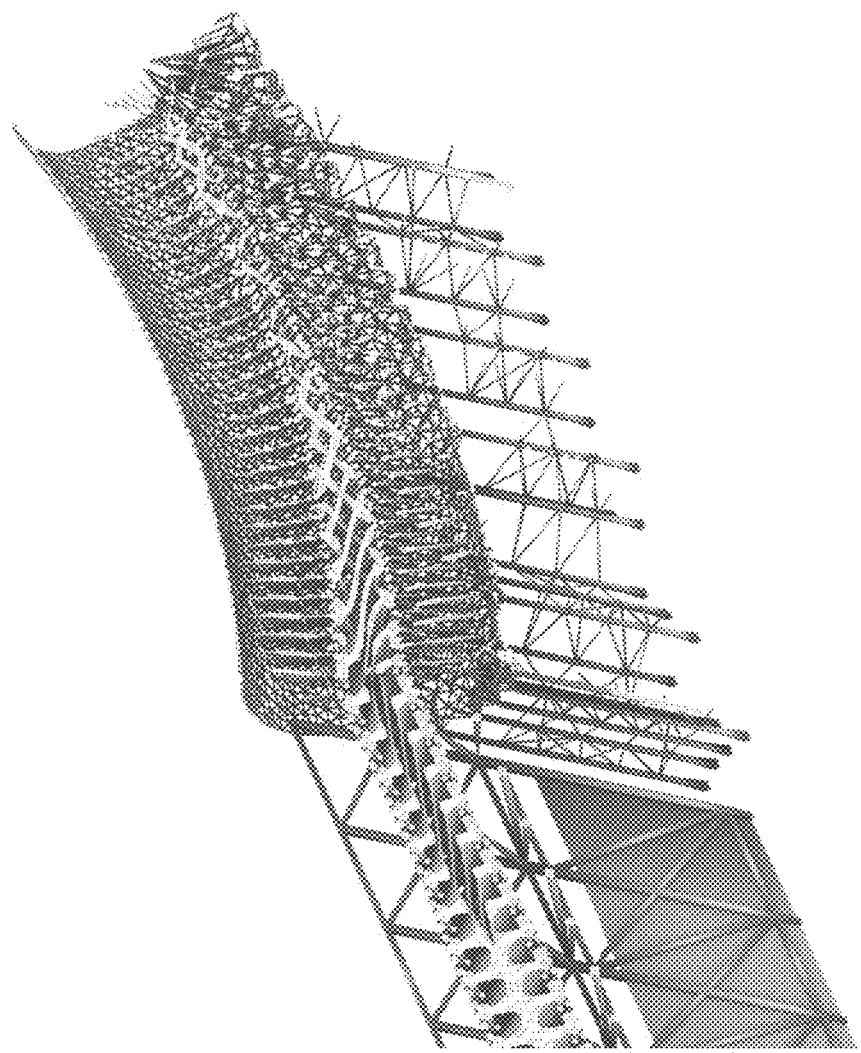

Cocoon structures also enable stacking of objects with fine structures, and other objects that require support structures that could land above one another. It prevents support from geometries above landing directly on fine structures. Instead, support coming down from above would land on the cocoon and load is transferred along the mesh structure. FIGS. 45A and 45B show examples of a cocoon support and cross section respectively.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be understood that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be understood that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be understood that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A 3D-printed swab or applicator, comprising
   a. a bulb having
      i. an interior lattice structure that provides structural strength and fluid retention,
      ii. a reinforced net structure upon the interior lattice structure that contributes to the shape of the bulb and absorbs fluid, and
      iii. a plurality of hairs projecting from the reinforced net structure; and
   b. a handle connected to the bulb, wherein the hairs are reinforced near their mid-section.

2. The 3D-printed swab or applicator of claim 1, wherein the hairs are arranged in a spiral array.

3. The 3D-printed swab or applicator of claim 1, wherein the interior lattice structure is contiguous between the bulb and the handle.

4. The 3D-printed swab or applicator of claim 1, wherein the interior lattice structure is printed by a shell offset from a free-form curve.

5. The 3D-printed swab or applicator of claim 1, wherein the hairs have a diameter less than about 100 μm.

6. The 3D-printed swab or applicator of claim 1, wherein the swab is defined by a data structure including a plurality of wire information, the wire information identifying a plurality of nodes that collectively identify at least one wire object.

7. The 3D-printed swab or applicator of claim 1, wherein the handle comprises parallel strands of wires and wherein the handle comprises a break point having a reduced diameter of the parallel strands of wires.

8. The 3D-printed swab or applicator of claim 1, wherein the handle comprises gridded shaft wall structures and an interior shearing reinforcement element.

9. The 3D-printed swab or applicator of claim 1, wherein the handle comprises parallel strands of wires and wherein the handle comprises a break point having a reduced diameter of the parallel strands of wires.

10. A 3D-printed swab or applicator, comprising
    a. a bulb having
       i. an interior lattice structure that provides structural strength and fluid retention,
       ii. a reinforced net structure upon the interior lattice structure that contributes to the shape of the bulb and absorbs fluid, and
       iii. a plurality of hairs projecting from the reinforced net structure; and
    b. a handle connected to the bulb, wherein the handle comprises parallel strands of wires which are bound together and reinforced by loops between the strands.

11. The 3D-printed swab or applicator of claim 10, wherein the hairs are reinforced near their mid-section.

12. The 3D-printed swab or applicator of claim 10, wherein the hairs are arranged in a spiral array.

13. The 3D-printed swab or applicator of claim 10, wherein the interior lattice structure is contiguous between the bulb and the handle.

14. The 3D-printed swab or applicator of claim 10, wherein the interior lattice structure is printed by a shell offset from a free-form curve.

15. The 3D-printed swab or applicator of claim 10, wherein the hairs have a diameter less than about 100 μm.

16. The 3D-printed swab or applicator of claim 10, wherein the swab is defined by a data structure including a plurality of wire information, the wire information identifying a plurality of nodes that collectively identify at least one wire object.

17. The 3D-printed swab or applicator of claim 10, wherein the handle comprises parallel strands of wires and wherein the handle comprises a break point having a reduced diameter of the parallel strands of wires.

18. The 3D-printed swab or applicator of claim 10, wherein the handle comprises gridded shaft wall structures and an interior shearing reinforcement element.

19. The 3D-printed swab or applicator of claim 10, wherein the handle comprises parallel strands of wires and wherein the handle comprises a break point having a reduced diameter of the parallel strands of wires.

20. A 3D-printed swab or applicator, comprising
    a. a bulb having
       i. an interior lattice structure that provides structural strength and fluid retention,
       ii. a reinforced net structure upon the interior lattice structure that contributes to the shape of the bulb and absorbs fluid, and
       iii. a plurality of hairs projecting from the reinforced net structure; and
    b. a handle connected to the bulb, wherein the handle comprises gridded shaft wall structures and an interior shearing reinforcement element.

21. The 3D-printed swab or applicator of claim 20, wherein the hairs are reinforced near their mid-section.

22. The 3D-printed swab or applicator of claim 20, wherein the hairs are arranged in a spiral array.

23. The 3D-printed swab or applicator of claim 20, wherein the interior lattice structure is contiguous between the bulb and the handle.

24. The 3D-printed swab or applicator of claim 20, wherein the interior lattice structure is printed by a shell offset from a free-form curve.

25. The 3D-printed swab or applicator of claim 20, wherein the hairs have a diameter less than about 100 μm.

26. The 3D-printed swab or applicator of claim 20, wherein the swab is defined by a data structure including a plurality of wire information, the wire information identifying a plurality of nodes that collectively identify at least one wire object.

27. The 3D-printed swab or applicator of claim 20, wherein the handle comprises parallel strands of wires and wherein the handle comprises a break point having a reduced diameter of the parallel strands of wires.

28. The 3D-printed swab or applicator of claim 20, wherein the handle comprises parallel strands of wires and wherein the handle comprises a break point having a reduced diameter of the parallel strands of wires.

29. A 3D-printed swab or applicator, comprising
   a. a bulb having
      i. an interior lattice structure that provides structural strength and fluid retention,
      ii. a reinforced net structure upon the interior lattice structure that contributes to the shape of the bulb and absorbs fluid, and
      iii. a plurality of hairs projecting from the reinforced net structure; and
   b. a handle connected to the bulb,
   wherein the handle comprises parallel strands of wires and wherein the handle comprises a break point having a reduced diameter of the parallel strands of wires.

30. The 3D-printed swab or applicator of claim 29, wherein the hairs are reinforced near their mid-section.

31. The 3D-printed swab or applicator of claim 29, wherein the hairs are arranged in a spiral array.

32. The 3D-printed swab or applicator of claim 29, wherein the interior lattice structure is contiguous between the bulb and the handle.

33. The 3D-printed swab or applicator of claim 29, wherein the interior lattice structure is printed by a shell offset from a free-form curve.

34. The 3D-printed swab or applicator of claim 29, wherein the hairs have a diameter less than about 100 μm.

35. The 3D-printed swab or applicator of claim 29, wherein the swab is defined by a data structure including a plurality of wire information, the wire information identifying a plurality of nodes that collectively identify at least one wire object.

36. The 3D-printed swab or applicator of claim 29, wherein the handle comprises gridded shaft wall structures and an interior shearing reinforcement element.

* * * * *